(12) United States Patent
Maruyama

(10) Patent No.: US 9,128,370 B2
(45) Date of Patent: Sep. 8, 2015

(54) RADIATION-SENSITIVE COMPOSITION AND COMPOUND

(71) Applicant: JSR Corporation, Tokyo (JP)

(72) Inventor: Ken Maruyama, Tokyo (JP)

(73) Assignee: JSR Corporation, Tokyo (JP)

( * ) Notice: Subject to any disclaimer, the term of this patent is extended or adjusted under 35 U.S.C. 154(b) by 71 days.

(21) Appl. No.: 13/759,118

(22) Filed: Feb. 5, 2013

(65) Prior Publication Data

US 2013/0149644 A1 Jun. 13, 2013

Related U.S. Application Data

(63) Continuation of application No. PCT/JP2011/066497, filed on Jul. 20, 2011.

(30) Foreign Application Priority Data

Aug. 17, 2010 (JP) ................................. 2010-182627

(51) Int. Cl.
  *G03F 7/004* (2006.01)
  *C07C 309/06* (2006.01)
  (Continued)

(52) U.S. Cl.
  CPC . *G03C 1/73* (2013.01); *C07C 25/18* (2013.01); *C07C 309/06* (2013.01);
  (Continued)

(58) Field of Classification Search
  None
  See application file for complete search history.

(56) References Cited

U.S. PATENT DOCUMENTS

| 4,491,628 A | 1/1985 | Ito et al. |
| 6,358,665 B1 | 3/2002 | Pawlowski et al. |

(Continued)

FOREIGN PATENT DOCUMENTS

| JP | 59-45439 | 3/1984 |
| JP | 2000-44535 | 2/2000 |

(Continued)

OTHER PUBLICATIONS

Perfluorooctyl Sulfonates; Proposed Significant New Use Rule, Federal Register, Oct. 18, 2000, p. 62319-p. 62333, vol. 65.

(Continued)

*Primary Examiner* — Cynthia H Kelly
*Assistant Examiner* — Alyssa L Cepluch
(74) *Attorney, Agent, or Firm* — Oblon, McClelland, Maier & Neustadt, L.L.P.

(57) ABSTRACT

A radiation-sensitive composition includes a photoacid generator represented by a general formula (1), and a solvent. Each $R^0$ independently represents a hydrogen atom, a fluorine atom, or a substituted or unsubstituted monovalent organic group. $R^1$ represents a fluorine atom or a substituted or unsubstituted monovalent organic group. $R^2$ represents a fluorine atom or a substituted or unsubstituted monovalent organic group. $R^f$ represents a fluoromethylene group or a divalent fluoroalkylene group. $M^+$ represents a monovalent onium cation. Optionally $R^1$ bonds to $R^f$ or $R^2$ to form a cyclic structure.

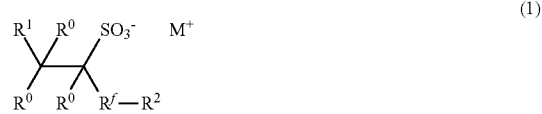

(1)

9 Claims, 1 Drawing Sheet

(51) Int. Cl.
*C07C 309/25* (2006.01)
*G03C 1/73* (2006.01)
*C07C 25/18* (2006.01)
*C07C 381/12* (2006.01)
*C07D 307/93* (2006.01)
*G03F 7/039* (2006.01)
*G03F 7/20* (2006.01)

(52) U.S. Cl.
CPC ............ *C07C 309/25* (2013.01); *C07C 381/12* (2013.01); *C07D 307/93* (2013.01); *G03F 7/0045* (2013.01); *G03F 7/0046* (2013.01); *G03F 7/0392* (2013.01); *G03F 7/0397* (2013.01); *G03F 7/2041* (2013.01); *C07C 2101/04* (2013.01); *C07C 2101/08* (2013.01); *C07C 2101/14* (2013.01); *C07C 2101/18* (2013.01)

(56) References Cited

U.S. PATENT DOCUMENTS

| | | | |
|---|---|---|---|
| 2002/0102491 A1* | 8/2002 | Kodama et al. | 430/270.1 |
| 2004/0009430 A1* | 1/2004 | Kanna et al. | 430/287.1 |
| 2005/0053861 A1* | 3/2005 | Yoneda et al. | 430/270.1 |
| 2005/0053961 A1 | 3/2005 | Akeson et al. | |
| 2007/0099114 A1* | 5/2007 | Watanabe et al. | 430/270.1 |
| 2009/0162787 A1* | 6/2009 | Seshimo et al. | 430/285.1 |
| 2009/0162788 A1* | 6/2009 | Hada et al. | 430/285.1 |

FOREIGN PATENT DOCUMENTS

| | | |
|---|---|---|
| JP | 2002-131897 | 5/2002 |
| JP | 2003-327572 | 11/2003 |
| JP | 2007-119678 A | 5/2007 |
| JP | 2008-083157 A | 4/2008 |
| JP | 2009-258585 A | 11/2009 |
| JP | 2010-138330 A | 6/2010 |
| JP | 2010-150234 A | 7/2010 |
| JP | 2012-013811 A | 1/2012 |
| WO | WO 00/08525 | 2/2000 |

OTHER PUBLICATIONS

Jiro Nakamura et al., "Resist Surface Roughness Calculated using Theoretical Percolation Model", J. Photopolym. Sci. Tech., 1998, p. 571-p. 576, vol. 11.
Eishi Shiobara et al., "Resist Edge Roughness with Reducing Pattern Size", Proc. SPIE, p. 313-p. 323, vol. 3333.
S.C. Palmateer, et al., "Line Edge Roughness in sub-0.18-μm Resist Patterns", Proc. SPIE, p. 634-p. 642, vol. 3333.
Hideo Namatsu et al., "Three-dimensional siloxane resist for the formation of nanopatterns with minimum linewidth fluctuations", J. Vac. Sci. Technol. B16 (1), 1998, p. 69-p. 76.
International Search Report for International Application No. PCT/JP2011/066497, Oct. 4, 2011.
Written Opinion for International Application No. PCT/JP2011/066497, Oct. 4, 2011.
Office Action issued Aug. 5, 2014 in Japanese Patent Application No. 2012-529528 (with English language translation).
Office Action issued Mar. 4, 2015, in Taiwan Patent Application No. 100128679 filed Aug. 11, 2011 (w/ English translation).

* cited by examiner

RADIATION-SENSITIVE COMPOSITION AND COMPOUND

CROSS-REFERENCE TO RELATED APPLICATIONS

The present application is a continuation application of International Application No. PCT/JP2011/066497, filed Jul. 20, 2011, which claims priority to Japanese Patent Application No. 2010-182627, filed Aug. 17, 2010. The contents of these applications are incorporated herein by reference in their entirety.

BACKGROUND OF THE INVENTION

1. Field of the Invention

The present invention relates to a radiation-sensitive composition and a compound.

2. Discussion of the Background

When deep ultraviolet rays (e.g., KrF excimer laser light or ArF excimer laser light) or the like are applied to a chemically-amplified radiation-sensitive resin composition, an acid is generated in the exposed area, and a difference in solubility rate in a developer occurs between the exposed area and the unexposed area due to chemical reactions catalyzed by the generated acid. A resist pattern is formed on a substrate by utilizing the difference in solubility rate (see Japanese Patent Application Publication (KOKAI) No. 59-45439 and Perfluorooctyl Sulfonates; Proposed Significant New Use Rule).

A photoacid generator included in the chemically-amplified radiation-sensitive resin composition is required to exhibit excellent transparency to radiation and have a high quantum yield when generating an acid. An acid generated by the photoacid generator is required to have sufficient acidity, a sufficiently high boiling point, and an appropriate diffusion distance (hereinafter may be referred to as "diffusion length") in the resist film, for example.

When using an ionic photoacid generator, the structure of the anion moiety is important in order to obtain sufficient acidity, a sufficiently high boiling point, and an appropriate diffusion length.

For example, a photoacid generator having a trifluoromethanesulfonyl structure generates an acid having sufficient acidity, and sufficiently increases the resolution of the photoresist.

A photoacid generator having a sulfonyl structure bonded to a large organic group (e.g., 10-camphorsulfonyl structure) generates an acid having a sufficiently high boiling point and an appropriate diffusion length (i.e., a sufficiently short diffusion length).

When precisely controlling the line width (e.g., when the device design dimensions are equal to or less than sub-half micrometers), it is important for a chemically-amplified resist to exhibit an excellent resolution and provide excellent surface flatness. When using a chemically-amplified resist that provides poor surface flatness, elevations and depressions (hereinafter may be referred to as "nano edge roughness") formed on the surface of the resist film may be transferred to a substrate when transferring the resist pattern to the substrate by etching or the like, so that the dimensional accuracy of the pattern may deteriorate. This may impair the electrical properties of the resulting device (see J. Photopolym. Sci. Tech., p. 571 (1998), Proc. SPIE, Vol. 3333, p. 313, Proc. SPIE, Vol. 3333, p. 634 and J. Vac. Sci. Technol. B16 (1), p. 69 (1998), for example).

SUMMARY OF THE INVENTION

According to one aspect of the present invention, a radiation-sensitive composition includes a photoacid generator represented by a general formula (1), and a solvent.

Each $R^0$ independently represents a hydrogen atom, a fluorine atom, or a substituted or unsubstituted monovalent organic group. $R^1$ represents a fluorine atom or a substituted or unsubstituted monovalent organic group. $R^2$ represents a fluorine atom or a substituted or unsubstituted monovalent organic group. $R^f$ represents a fluoromethylene group or a divalent fluoroalkylene group. $M^+$ represents a monovalent onium cation. Optionally $R^1$ bonds to $R^f$ or $R^2$ to form a cyclic structure.

According to another aspect of the present invention, a compound is represented by a general formula (1).

Each $R^0$ independently represents a hydrogen atom, a fluorine atom, or a substituted or unsubstituted monovalent organic group. $R^1$ represents a fluorine atom or a substituted or unsubstituted monovalent organic group. $R^2$ represents a fluorine atom or a substituted or unsubstituted monovalent organic group. $R^f$ represents a fluoromethylene group or a divalent fluoroalkylene group. $M^+$ represents a monovalent onium cation. Optionally $R^1$ bonds to $R^f$ or $R^2$ to form a cyclic structure.

According to further aspect of the present invention, a compound is represented by a general formula (2).

$R^1$ represents a fluorine atom or a substituted or unsubstituted monovalent organic group. $R^2$ represents a fluorine atom or a substituted or unsubstituted monovalent organic group. $R^f$ represents a fluoromethylene group or a divalent fluoroalkylene group. $M^+$ represents a monovalent onium cation. Optionally $R^1$ bonds to $R^f$ or $R^2$ to form a cyclic structure.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

Figure 1:
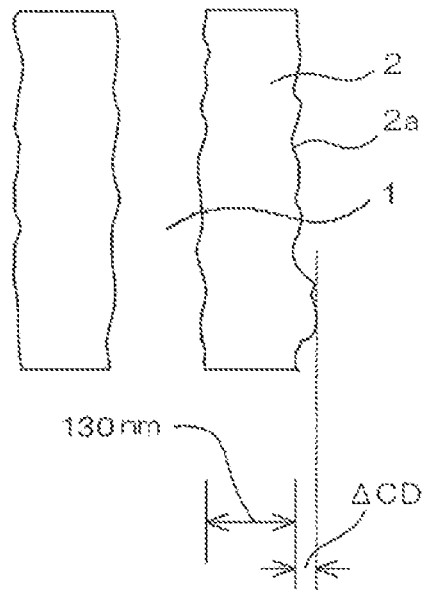
FIG. 1 is a schematic plan view illustrating a line pattern.

Embodiments of the present invention are as follows:
1. A radiation-sensitive composition including a photoacid generator represented by a general formula (1), and a solvent,

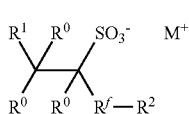

(1)

wherein $R^0$ independently represent a hydrogen atom, a fluorine atom, or a substituted or unsubstituted monovalent organic group, $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.

(2) The radiation-sensitive composition according to (1), wherein the photoacid generator is a compound represented by a general formula (2),

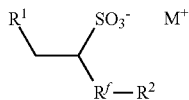

(2)

wherein $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.

(3) The radiation-sensitive composition according to (1) or (2), wherein $R^1$ represents (b1) a linear or branched monovalent hydrocarbon group having 1 to 30 carbon atoms, some or all of the hydrogen atoms of the hydrocarbon group being substituted with a fluorine atom, (b2) the hydrocarbon group as defined in (b1) that further includes an ether bond or a sulfide bond, (b3) a cyclic or cyclic structure-containing monovalent aliphatic hydrocarbon group having 3 to 30 carbon atoms, some or all of the hydrogen atoms of the aliphatic hydrocarbon group being substituted with a fluorine atom, (b4) a group obtained by substituting a ring carbon atom of the aliphatic hydrocarbon group as defined in (b3) with an oxygen atom or a sulfur atom, or (b5) an aryl group having 6 to 30 carbon atoms, some or all of the hydrogen atoms of the aryl group being substituted with at least a fluorine atom.

(4) The radiation-sensitive composition according to (1) or (2), wherein $R^1$ represents (b1) a linear or branched monovalent hydrocarbon group having 1 to 30 carbon atoms, some or all of the hydrogen atoms of the hydrocarbon group being substituted with a fluorine atom, (b2) the hydrocarbon group as defined in (b1) that further includes an ether bond or a sulfide bond, (b4) a group obtained by substituting a ring carbon atom of a cyclic or cyclic structure-containing monovalent aliphatic hydrocarbon group having 3 to 30 carbon atoms, some or all of the hydrogen atoms of the aliphatic hydrocarbon group being substituted with a fluorine atom with an oxygen atom or a sulfur atom, or (b5) an aryl group having 6 to 30 carbon atoms, some or all of the hydrogen atoms of the aryl group being substituted with at least a fluorine atom.

(5) The radiation-sensitive composition according to (1) or (2), wherein $R^1$ represents (b1) a linear or branched monovalent hydrocarbon group having 1 to 30 carbon atoms, some or all of the hydrogen atoms of the hydrocarbon group being substituted with a fluorine atom, or (b2) the hydrocarbon group as defined in (b1) that further includes an ether bond or a sulfide bond.

(6) The radiation-sensitive composition according to (1) or (2), wherein $R^1$ represents (b1) a linear or branched monovalent hydrocarbon group having 1 to 30 carbon atoms, some or all of the hydrogen atoms of the hydrocarbon group being substituted with a fluorine atom.

(7) The radiation-sensitive composition according to any one of (1) to (6), wherein the monovalent onium cation ($M^+$) is a sulfonium cation represented by a general formula (m1-1),

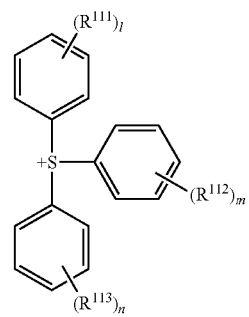

(m1-1)

wherein $R^{111}$ to $R^{113}$ independently represent a hydroxyl group, a halogen atom, a substituted or unsubstituted alkyl group, a substituted or unsubstituted cycloalkyl group, a substituted or unsubstituted alkoxy group, —S—$R^{114}$ (wherein $R^{114}$ represents a substituted or unsubstituted alkyl group or a substituted or unsubstituted aryl group), or —SO$_2$—$R^{115}$ (wherein $R^{115}$ represents a substituted or unsubstituted alkyl group, a substituted or unsubstituted cycloalkyl group, a substituted or unsubstituted alkoxy group, or a substituted or unsubstituted aryl group), provided that at least one $R^{111}$ represents —SO$_2$—$R^{115}$, l is an integer from 1 to 5, m is an integer from 0 to 5, and n is an integer from 0 to 5.

(8) The radiation-sensitive composition according to any one of (1) to (7), further including a resin that includes at least one repeating unit among repeating units respectively represented by general formulas (b-1) to (b-5),

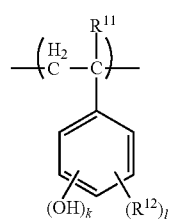

(b-1)

wherein $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, provided that k+l≤5 is satisfied,

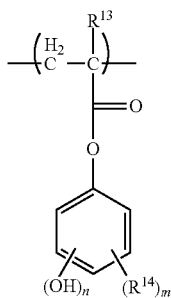
(b-2)

wherein $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, provided that m+n≤5 is satisfied,

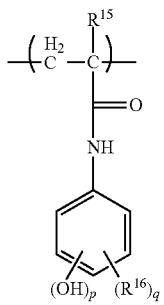
(b-3)

wherein $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, provided that p+q≤5 is satisfied,

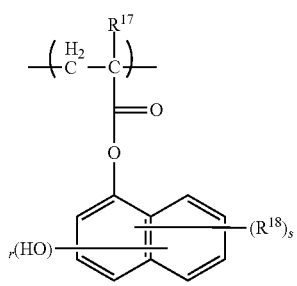
(b-4)

wherein $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3,

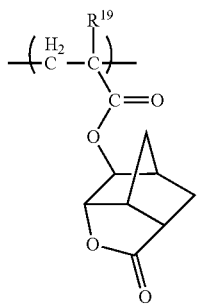
(b-5)

wherein $R^{19}$ represents a hydrogen atom or a methyl group.

(9) A compound represented by a general formula (1),

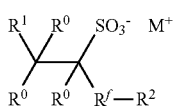
(1)

wherein $R^0$ independently represent a hydrogen atom, a fluorine atom, or a substituted or unsubstituted monovalent organic group, $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.

(10) A compound represented by a general formula (2),

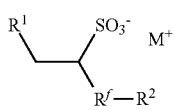
(2)

wherein $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.

(11) The compound according to (9) or (10), wherein $R^1$ represents (b1) a linear or branched monovalent hydrocarbon group having 1 to 30 carbon atoms, some or all of the hydrogen atoms of the hydrocarbon group being substituted with a fluorine atom, (b2) the hydrocarbon group as defined in (b1) that further includes an ether bond or a sulfide bond, (b3) a cyclic or cyclic structure-containing monovalent aliphatic hydrocarbon group having 3 to 30 carbon atoms, some or all of the hydrogen atoms of the aliphatic hydrocarbon group being substituted with a fluorine atom, (b4) a group obtained by substituting a ring carbon atom of the aliphatic hydrocarbon group as defined in (b3) with an oxygen atom or a sulfur atom, or (b5) an aryl group having 6 to 30 carbon atoms, some or all of the hydrogen atoms of the aryl group being substituted with at least a fluorine atom.

The embodiment of this invention includes a radiation-sensitive composition that includes an onium sulfonate (sulfonic acid onium salt) having a specific structure.

The radiation-sensitive composition according to the embodiment of the invention may produce a chemically-amplified positive-tone resist film that effectively responds to (extreme) deep ultraviolet rays (e.g., KrF excimer laser light, ArF excimer laser light, or EUV), X-rays such as synchrotron radiation, or electron beams, shows only a small degree of nano edge roughness, exhibits excellent sensitivity and resolution, and stably and accurately produces a fine pattern.

The novel compound according to the embodiment of the invention exhibits high solubility in a solvent, and may suitably be used as the photoacid generator included in the radiation-sensitive composition according to the embodiment of the invention.

The embodiments will now be described with reference to the accompanying drawings, wherein like reference numerals designate corresponding or identical elements throughout the various drawings. Note that the invention is not limited to the following exemplary embodiments. It should be understood that various modifications, improvements, and the like may be made of the following exemplary embodiments without departing from the scope of the invention based on common knowledge of a person skilled in the art.

The term "(meth)acrylate" used herein refers to "acrylate" or "methacrylate".

[1] Radiation-Sensitive Composition

A radiation-sensitive composition according to one embodiment of the invention includes a specific photoacid generator and a solvent.

[1-1] Photoacid Generator (A)

The photoacid generator (hereinafter may be referred to as "acid generator (A)") is a compound represented by the general formula (1). The acid generator (A) exhibits high solubility in a solvent. A radiation-sensitive composition that includes the acid generator (A) can form a resist film that can produce an excellent resist pattern. The acid generator (A) rarely volatilizes during a photolithographic process due to a high boiling point, and generates an acid that exhibits a short acid diffusion length in the resist film. Specifically, the acid generator (A) generates an acid that exhibits a moderate acid diffusion length.

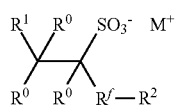

(1)

(In the general formula (1), $R^0$ independently represent a hydrogen atom, a fluorine atom, or a substituted or unsubstituted monovalent organic group, $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.)

The compound represented by the general formula (1) is preferably a compound represented by the following general formula (2).

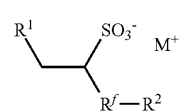

(2)

(In the general formula (2), $R^1$ represents a fluorine atom or a substituted or unsubstituted monovalent organic group, provided that $R^1$ may bond to $R^f$ or $R^2$ to form a cyclic structure, $R^2$ represents a fluorine atom or a substituted or unsubstituted monovalent organic group, $R^f$ represents a fluoromethylene group or a divalent fluoroalkylene group, and $M^+$ represents a monovalent onium cation.)

Examples of the monovalent organic group represented by $R^0$ in the general formula (1) include substituted or unsubstituted linear or branched hydrocarbon groups having 1 to 30 carbon atoms, and the like.

Examples of the unsubstituted linear or branched monovalent hydrocarbon group having 1 to 30 carbon atoms represented by $R^0$ in the general formula (1) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, an n-dodecyl group, and the like.

Examples of a substituent that may substitute the linear or branched monovalent hydrocarbon group having 1 to 30 carbon atoms include a halogen atom (e.g., fluorine atom, chlorine atom, bromine atom, or iodine atom), a hydroxyl group, a thiol group, an aryl group, an alkenyl group, an organic group (e.g., alkyl group) that includes a heteroatom (e.g., halogen atom, oxygen atom, nitrogen atom, sulfur atom, phosphorus atom, or silicon atom), and the like. The linear or branched monovalent hydrocarbon group having 1 to 30 carbon atoms may be substituted with a keto group (i.e., two hydrogen atoms bonded to a single carbon atom of the hydrocarbon group are substituted with an oxygen atom). The number of substituents is not particularly limited.

Examples of the substituted linear or branched monovalent hydrocarbon group having 1 to 30 carbon atoms include a benzyl group, a methoxymethyl group, a methylthiomethyl group, an ethoxymethyl group, a phenoxymethyl group, a methoxycarbonylmethyl group, an ethoxycarbonylmethyl group, an acetylmethyl group, a fluoromethyl group, a trifluoromethyl group, a 2,2,2-trifluoroethyl group, a chloromethyl group, a trichloromethyl group, a 2-fluoropropyl group, a trifluoroacetylmethyl group, a trichloroacetylmethyl group, a pentafluorobenzoylmethyl group, an aminomethyl group, a cyclohexylaminomethyl group, a diphenylphosphinomethyl group, a trimethylsilylmethyl group, a 2-phenylethyl group, a 3-phenylpropyl group, a 2-aminoethyl group, a hydroxymethyl group, a hydroxyethyl group, a hydroxycarbonylmethyl group, and the like.

Examples of the unsubstituted linear or branched monovalent hydrocarbon group represented by $R^1$ in the general formulas (1) and (2) include (b0) a linear or branched monovalent hydrocarbon group having 1 to 30 carbon atoms, (b1) a linear or branched monovalent hydrocarbon group having 1 to 30 carbon atoms, some or all of the hydrogen atoms of the hydrocarbon group being substituted with a fluorine atom, (b2) the hydrocarbon group as defined in (b1) that further includes an ether bond or a sulfide bond, (b3) a cyclic or cyclic structure-containing monovalent aliphatic hydrocarbon group having 3 to 30 carbon atoms, some or all of the hydrogen atoms of the aliphatic hydrocarbon group being substituted with a fluorine atom, (b4) a group obtained by substituting a ring carbon atom of the aliphatic hydrocarbon group as defined in (b3) with an oxygen atom or a sulfur atom, (b5) an aryl group having 6 to 30 carbon atoms, some or all of the hydrogen atoms of the aryl group being substituted with at least a fluorine atom, and the like.

Examples of the linear or branched monovalent hydrocarbon group having 1 to 30 carbon atoms as defined in (b0) include those mentioned above in connection with $R^0$ in the general formula (1).

Examples of the linear or branched monovalent hydrocarbon group having 1 to 30 carbon atoms as defined in (b1) (some or all of the hydrogen atoms of the hydrocarbon group are substituted with a fluorine atom) include a group obtained by substituting some or all of the hydrogen atoms of the hydrocarbon group as defined in (b0) with a fluorine atom.

Examples of the hydrocarbon group as defined in (b2) that further includes an ether bond or a sulfide bond include a group obtained by introducing at least one ether bond or sulfide bond into the hydrocarbon group as defined in (b1).

Examples of the cyclic or cyclic structure-containing monovalent aliphatic hydrocarbon group having 3 to 30 carbon atoms as defined in (b3) (some or all of the hydrogen atoms of the aliphatic hydrocarbon group are substituted with a fluorine atom) include a cyclopropyl group, a cyclobutyl group, a cyclopentyl group, a cyclohexyl group, a bornyl group, a norbornyl group, an adamantyl group, a pinanyl group, a thujyl group, a caryl group, a camphanyl group, a cyclopropylmethyl group, a cyclobutylmethyl group, a cyclopentylmethyl group, a cyclohexylmethyl group, a bornylmethyl group, a norbornylmethyl group, an adamantylmethyl group, and the like.

Examples of a substituent that may substitute the aliphatic hydrocarbon group include those mentioned above. Examples of the substituted cyclic or cyclic structure-containing monovalent aliphatic hydrocarbon group having 3 to 30 carbon atoms include a 4-fluorocyclohexyl group, a 4-hydroxycyclohexyl group, a 4-methoxycyclohexyl group, a 4-methoxycarbonylcyclohexyl group, a 3-hydroxy-1-adamantyl group, a 3-methoxycarbonyl-1-adamantyl group, a 3-hydroxycarbonyl-1-adamantyl group, a 3-hydroxymethyl-1-adamantanemethyl group, and the like.

Examples of the group as defined in (b4) that is obtained by substituting a ring carbon atom of the aliphatic hydrocarbon group as defined in (b3) with an oxygen atom or a sulfur atom include a group obtained by substituting a ring carbon atom of the aliphatic hydrocarbon group as defined in (b3) with an oxygen atom or a sulfur atom, and the like.

Examples of the aryl group having 6 to 30 carbon atoms as defined in (b5) (some or all of the hydrogen atoms of the aryl group are substituted with at least a fluorine atom) include a group obtained by substituting some or all of the hydrogen atoms of the aryl group (e.g., phenyl group, 1-naphthyl group, 2-naphthyl group, 1-anthryl group, or 1-phenanthryl group) with a fluorine atom.

The aryl group may also be substituted with a substituent other than a fluorine atom. Examples of such a substituent include a halogen atom (e.g., fluorine atom, chlorine atom, bromine atom, and iodine atom), a hydroxyl group, a thiol group, an alkyl group, an organic group that includes a heteroatom (e.g., halogen atom, oxygen atom, nitrogen atom, sulfur atom, phosphorus atom, or silicon atom), and the like.

It is preferable that $R^1$ represent one of the groups as defined in (b1), (b2), (b4), and (b5). Further, it is preferable that $R^1$ represent one of the groups as defined in (b1) and (b2). It is particularly preferable that $R^1$ represent the group as defined in (b1).

Examples of the substituted or unsubstituted monovalent organic group represented by $R^2$ in the general formulas (1) and (2) include (c1) a substituted or unsubstituted linear or branched monovalent hydrocarbon group having 1 to 30 carbon atoms, (c2) the hydrocarbon group as defined in (c1) that further includes an ether bond or a sulfide bond, (c3) a cyclic or cyclic structure-containing monovalent aliphatic hydrocarbon group having 3 to 30 carbon atoms, (c4) a group obtained by substituting a ring carbon atom of the aliphatic hydrocarbon group as defined in (c3) with an oxygen atom or a sulfur atom, (c5) an aryl group having 6 to 30 carbon atoms, and the like.

Examples of the substituted or unsubstituted linear or branched monovalent hydrocarbon group having 1 to 30 carbon atoms as defined in (c1) include those mentioned above in connection with $R^0$ (provided that a group that includes a halogen atom as a substituent is excluded).

Examples of the hydrocarbon group as defined in (c2) that further includes an ether bond or a sulfide bond include a group obtained by introducing at least one ether bond or sulfide bond into the hydrocarbon group as defined in (c1).

Examples of the cyclic or cyclic structure-containing monovalent aliphatic hydrocarbon group having 3 to 30 carbon atom as defined in (c3) include the unsubstituted aliphatic hydrocarbon group as defined in (b3), and the like. The aliphatic hydrocarbon group may be substituted with a substituent. Examples of a substituent that may substitute the aliphatic hydrocarbon group include a halogen atom (e.g., fluorine atom, chlorine atom, bromine atom, or iodine atom), a hydroxyl group, a thiol group, an aryl group, an alkenyl group, an organic group (e.g., alkyl group) that includes a heteroatom (e.g., oxygen atom, nitrogen atom, sulfur atom, phosphorus atom, or silicon atom), and the like.

Examples of the group as defined in (c4) that is obtained by substituting a ring carbon atom of the aliphatic hydrocarbon group as defined in (c3) with an oxygen atom or a sulfur atom include a group obtained by substituting a ring carbon atom of the aliphatic hydrocarbon group as defined in (c3) with an oxygen atom or a sulfur atom, and the like.

Examples of the aryl group having 6 to 30 carbon atoms as defined in (c5) include a phenyl group, a 1-naphthyl group, a 2-naphthyl group, a 1-anthryl group, a 1-phenanthryl group, and the like. Examples of a substituent that may substitute the aryl group include a halogen atom (e.g., fluorine atom, chlorine atom, bromine atom, and iodine atom), a hydroxyl group, a thiol group, an alkyl group, an organic group that includes a heteroatom (e.g., oxygen atom, nitrogen atom, sulfur atom, phosphorus atom, or silicon atom), and the like.

Examples of the divalent fluoroalkylene group represented by $R^f$ in the general formulas (1) and (2) include a group obtained by substituting an arbitrary hydrogen atom of the unsubstituted linear or branched monovalent hydrocarbon group having 1 to 30 carbon atoms represented by $R^1$ with a fluorine atom.

It is particularly preferable that $R^f$ is a difluoromethylene group or a divalent perfluoroalkylene group.

When $R^1$ in the general formulas (1) and (2) bonds to $R^f$ or $R^2$ to form a cyclic structure, $R^1$ represents a methylene group, a linear or branched alkylene group having 2 to 18 (preferably 2 to 10) carbon atoms, a fluoromethylene group, or a linear or branched fluoroalkylene group having 2 to 18 (preferably 2 to 10) carbon atoms. $R^2$ represents a fluorine atom, a methylene group, or a linear or branched alkylene group having 2 to 18 (preferably 2 to 10) carbon atoms. $R^f$ represents a fluoromethylene group or a linear or branched fluoroalkylene group having 2 to 18 (preferably 2 to 10) carbon atoms.

Examples of the compound represented by the general formula (1) or (2) include compounds represented by the following formula (A1) to (A38), and the like. Note that M⁺ (monovalent onium cation) in each formula is described below.
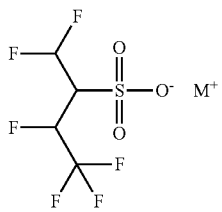
(A1)
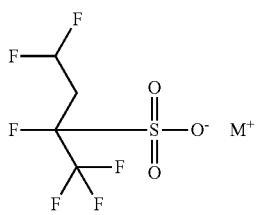
(A2)
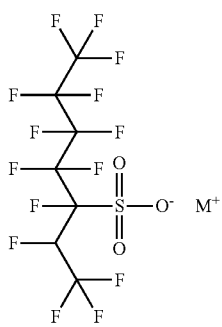
(A3)
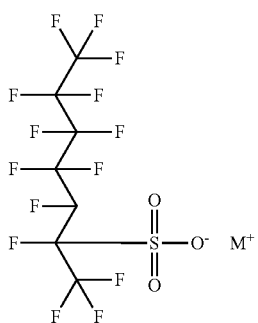
(A4)
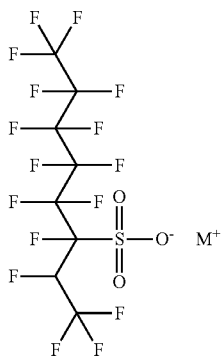
(A5)
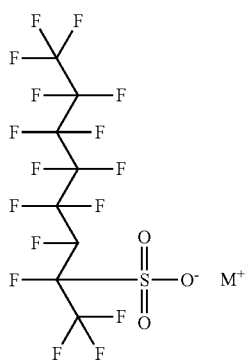
(A6)
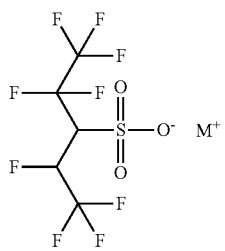
(A7)
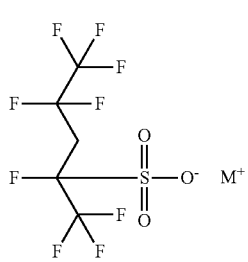
(A8)
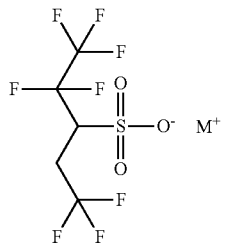
(A9)
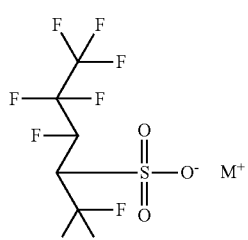
(A10)
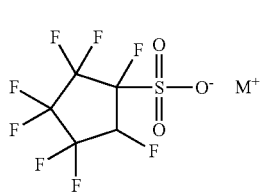
(A11)

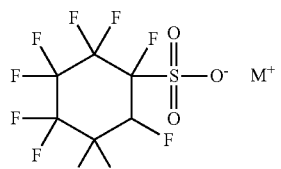
(A12)
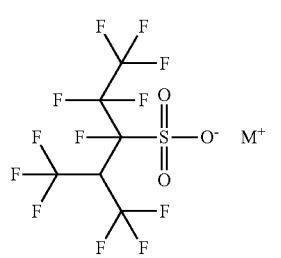
(A13)
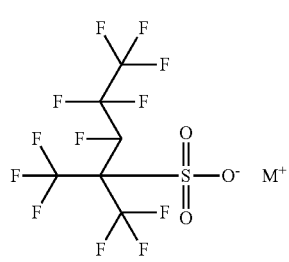
(A14)
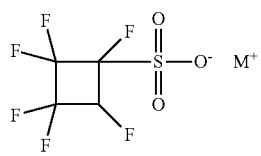
(A15)
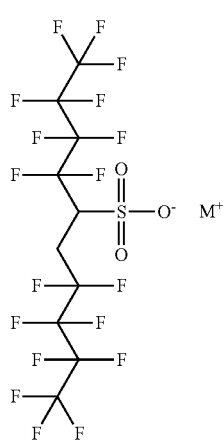
(A16)
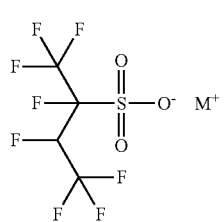
(A17)
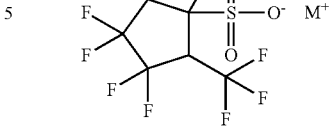
(A18)
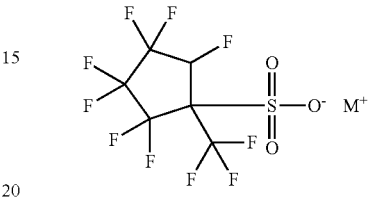
(A19)
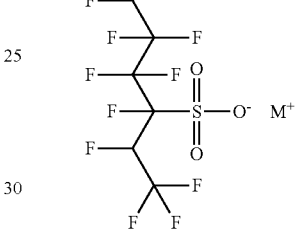
(A20)
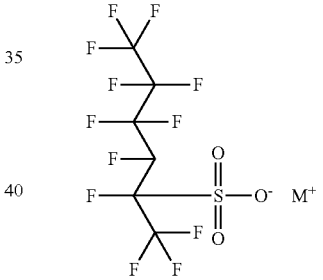
(A21)
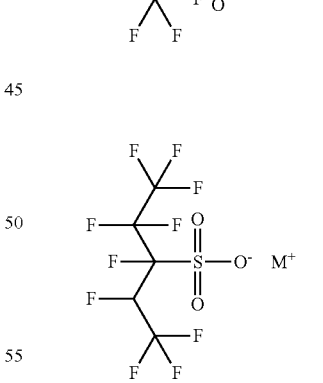
(A22)
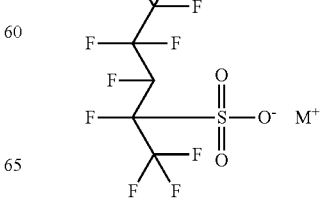
(A23)

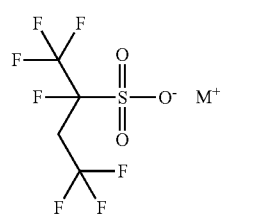 (A24)
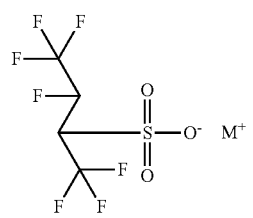 (A25)
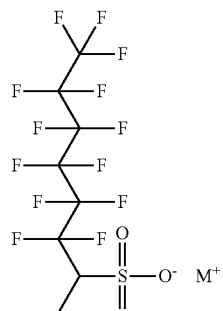 (A26)
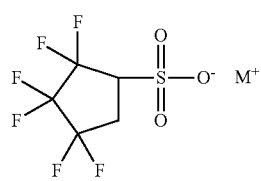 (A27)
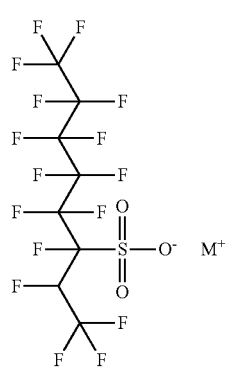 (A28)
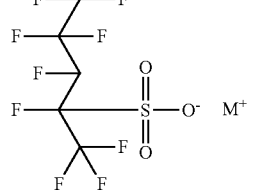 (A29)
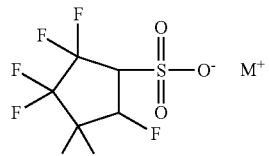 (A30)
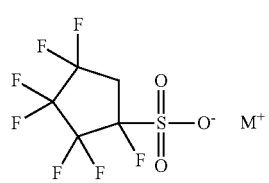 (A31)
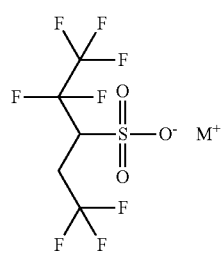 (A32)
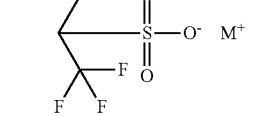 (A33)
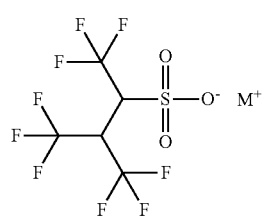 (A34)

-continued

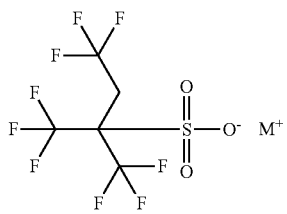 (A35)

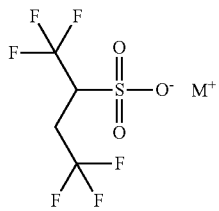 (A36)

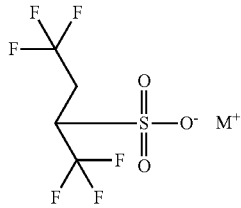 (A37)

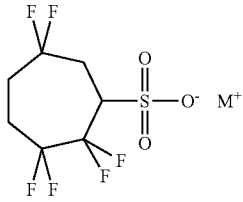 (A38)

Specific examples of the sulfonium cation (onium cation of S) include a sulfonium cation represented by the following general formula (m1). Specific examples of the iodonium cation (onium cation of I) include an iodonium cation represented by the following general formula (m2).

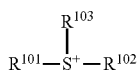 (m1)

(In the general formula (m1), $R^{101}$, $R^{102}$, and $R^{103}$ independently represent a substituted or unsubstituted linear or branched alkyl group having 1 to 10 carbon atoms or a substituted or unsubstituted aryl group having 6 to 18 carbon atoms, or two of $R^{101}$, $R^{102}$ and $R^{103}$ bond to each other to form a cyclic structure together with the sulfur atom, and the remainder of $R^{101}$, $R^{102}$, and $R^{103}$ represents a substituted or unsubstituted linear or branched alkyl group having 1 to 10 carbon atoms or a substituted or unsubstituted aryl group having 6 to 18 carbon atoms.)

$R^{104}$—$I^+$—$R^{105}$ (m2)

(In the general formula (m2), $R^{104}$ and $R^{105}$ independently represent a substituted or unsubstituted linear or branched alkyl group having 1 to 10 carbon atoms or a substituted or unsubstituted aryl group having 6 to 18 carbon atoms, or bond to each other to form a cyclic structure together with the iodine atom.)

Examples of the unsubstituted linear or branched alkyl group having 1 to 10 carbon atoms represented by $R^{101}$ to $R^{103}$ in the general formula (m1) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, and the like.

The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the aryl group having 6 to 18 carbon atoms represented by $R^{101}$ to $R^{103}$ in the general formula (m1) include a phenyl group, a 1-naphthyl group, a 2-naphthyl group, a 1-anthryl group, a 1-phenanthryl group, and the like.

The aryl group may be substituted with a halogen atom (e.g., fluorine atom, chlorine atom, bromine atom, or iodine atom), a hydroxyl group, a thiol group, an alkyl group, an alkoxy group, an organic group that includes a heteroatom (e.g., halogen atom, oxygen atom, nitrogen atom, sulfur atom, phosphorus atom, or silicon atom), or the like.

An onium cation represented by the following general formula (m1-1) or (m1-2) is preferable as the onium cation represented by the general formula (m1). The following onium cation represented by the general formula (m1-1) is particularly preferable.

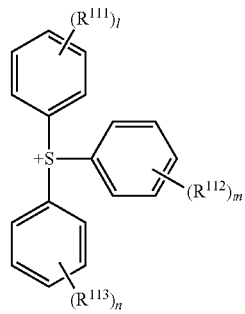 (m1-1)

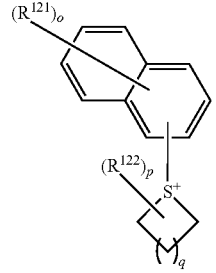 (m1-2)

In the general formula (m1-1), $R^{111}$ to $R^{113}$ independently represent a hydroxyl group, a halogen atom, a substituted or unsubstituted alkyl group, a substituted or unsubstituted cycloalkyl group, a substituted or unsubstituted alkoxy group, —S—$R^{114}$ (wherein $R^{114}$ represents a substituted or unsubstituted alkyl group or a substituted or unsubstituted aryl group), or —SO$_2$—$R^{115}$ (wherein $R^{115}$ represents a substituted or unsubstituted alkyl group, a substituted or unsubstituted cycloalkyl group, a substituted or unsubstituted alkoxy group, or a substituted or unsubstituted aryl group), provided that at least one $R^{111}$ represents —$SO_2$—$R^{115}$, l is an integer from 1 to 5, m is an integer from 0 to 5, and n is an integer from 0 to 5.

In the general formula (m1-2), $R^{121}$ represents a substituted or unsubstituted linear or branched alkyl group having 1 to 8 carbon atoms or a substituted or unsubstituted aryl group having 6 to 8 carbon atoms, or two or more $R^{121}$ bond to each other to form a ring, provided that a plurality of $R^{121}$ may be either identical or different when a plurality of $R^{121}$ are present.

$R^{122}$ represents a substituted or unsubstituted linear or branched alkyl group having 1 to 7 carbon atoms or a substituted or unsubstituted aryl group having 6 or 7 carbon atoms, or two or more $R^{122}$ bond to each other to form a ring, provided that a plurality of $R^{122}$ may be either identical or different when a plurality of $R^{122}$ are present.

o is an integer from 0 to 7, p is an integer from 0 to 6, and q is an integer from 0 to 3.

Examples of the halogen atom represented by $R^{111}$ to $R^{113}$ in the general formula (m1-1) include a fluorine atom, a chlorine atom, a bromine atom, an iodine atom, and the like.

The alkyl group represented by $R^{111}$ to $R^{113}$ is preferably a linear or branched alkyl group having 1 to 4 carbon atoms.

Examples of the cycloalkyl group represented by $R^{111}$ to $R^{113}$ include a cyclopropyl group, a cyclobutyl group, a cyclopentyl group, a cyclohexyl group, a cycloheptyl group, a cyclooctyl group, and the like. Among these, a cycloalkyl group having 5 or 6 carbon atoms is preferable.

The alkoxy group represented by $R^{111}$ to $R^{113}$ is preferably an alkoxy group having 1 to 4 carbon atoms.

Note that one or more hydrogen atoms of the alkyl group, the cycloalkyl group, and the alkoxy group may be substituted with a substituent. Specific examples of the substituent include a halogen atom (e.g., fluorine atom, chlorine atom, and bromine atom), a phenyl group, an acetoxy group, an alkyl group, an alkoxy group, and the like.

Examples of the alkyl group represented by $R^{114}$ of —S—$R^{114}$ represented by $R^{111}$ to $R^{113}$ include those mentioned above in connection with $R^{111}$ to $R^{113}$.

Examples of the aryl group represented by $R^{114}$ include a phenyl group, a 1-naphthyl group, a 2-naphthyl group, a 1-anthryl group, a 1-phenanthryl group, and the like. Among these, an aryl group having 6 to 12 carbon atoms is preferable.

Note that one or more hydrogen atoms of the alkyl group and the aryl group represented by $R^{114}$ may be substituted with a substituent. Examples of the substituent include those mentioned above.

Examples of the substituted or unsubstituted alkyl group, the substituted or unsubstituted cycloalkyl group, the substituted or unsubstituted alkoxy group, or the substituted or unsubstituted aryl group represented by $R^{115}$ of —$SO_2$—$R^{115}$ include those mentioned above in connection with $R^{111}$ to $R^{114}$.

Specific examples of the group represented by —$SO_2$—$R^{115}$ include groups respectively represented by the following formulas (h1) to (h8), and the like. Among these, the groups respectively represented by the formulas (h1) and (h2) are preferable.

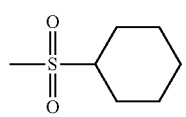

(h1)

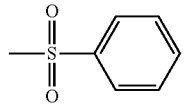

(h2)

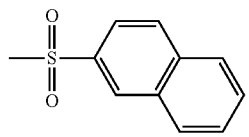

(h3)

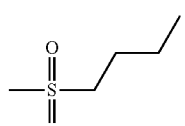

(h4)

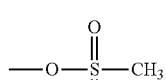

(h5)

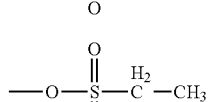

(h6)

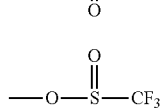

(h7)

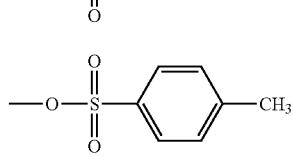

(h8)

Examples of a substituent that may substitute the linear or branched alkyl group having 1 to 8 carbon atoms represented by $R^{121}$ in the general formula (m1-2) include a halogen atom (e.g., fluorine atom, chlorine atom, bromine atom, and iodine atom), a hydroxyl group, a thiol group, and an organic group that includes a heteroatom (e.g., halogen atom, oxygen atom, nitrogen atom, sulfur atom, phosphorus atom, or silicon atom).

Examples of the aryl group having 6 to 8 carbon atoms represented by $R^{121}$ include a phenyl group, a phenyl group that is substituted with a substituent mentioned above in connection with the alkyl group having 1 to 8 carbon atoms, and the like.

Examples of a substituent that may substitute the linear or branched alkyl group having 1 to 7 carbon atoms represented by $R^{122}$ in the general formula (m1-2) include those mentioned above in connection with the alkyl group having 1 to 8 carbon atoms.

Examples of the aryl group having 6 or 7 carbon atoms represented by $R^{122}$ include a phenyl group, a phenyl group that is substituted with a substituent mentioned above in connection with the alkyl group having 1 to 8 carbon atoms, and the like.

The sulfonium cations respectively represented by the following formulas (i-1) to (i-13) are preferable as the sulfonium cation represented by the general formula (m1).

(i-1)
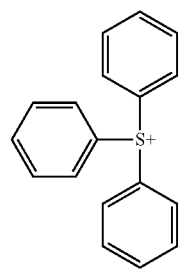
(i-2)
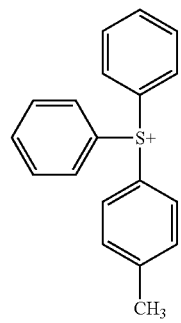
(i-3)
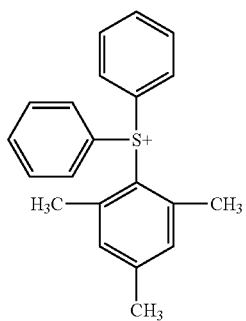
(i-4)
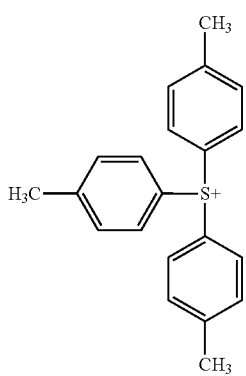
-continued
(i-5)
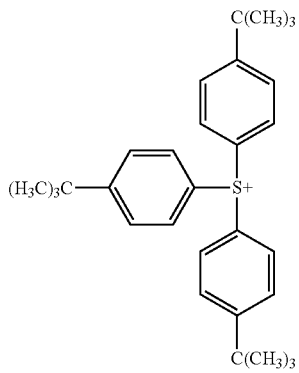
(i-6)
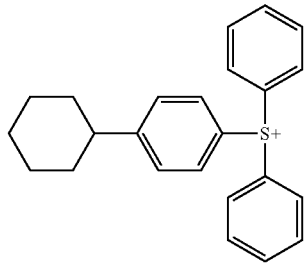
(i-7)
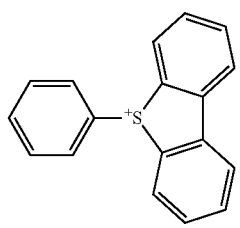
(i-8)
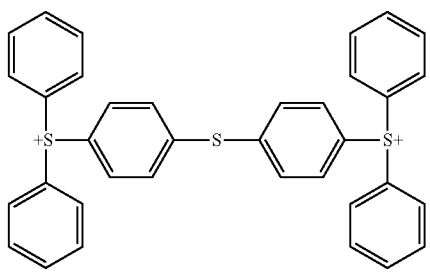
(i-9)

(i-10)
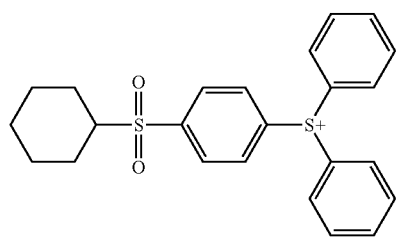

(i-11)
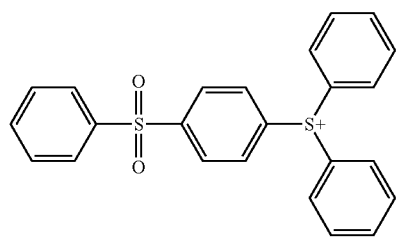

(i-12)
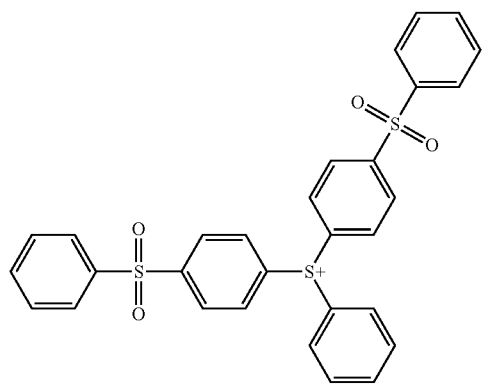

(i-13)
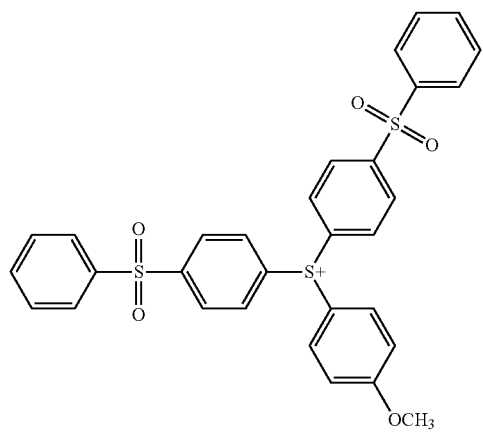

The linear or branched alkyl group having 1 to 10 carbon atoms represented by $R^{104}$ and $R^{105}$ in the general formula (m2) may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the unsubstituted aryl group having 6 to 18 carbon atoms represented by $R^{104}$ and $R^{105}$ in the general formula (m2) include a phenyl group, a 1-naphthyl group, a 2-naphthyl group, a 1-anthryl group, a 1-phenanthryl group, and the like.

The aryl group may be substituted with a substituent mentioned above in connection with the linear or branched alkyl group having 1 to 10 carbon atoms.

An onium cation represented by the following general formula (m2-1) is preferable as the onium cation represented by the general formula (m2).

(m2-1)
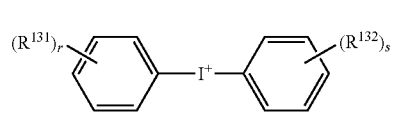

In the general formula (m2-1), $R^{131}$ and $R^{132}$ independently represent a hydrogen atom, a substituted or unsubstituted linear or branched alkyl group having 1 to 12 carbon atoms, or a substituted or unsubstituted aryl group having 6 to 12 carbon atoms, or two or more of $R^{131}$ and $R^{132}$ bond to form a ring, provided that a plurality of $R^{131}$ may be either identical or different when a plurality of $R^{131}$ are present, and a plurality of $R^{132}$ may be either identical or different when a plurality of $R^{132}$ are present.

r is an integer from 0 to 5, and s is an integer from 0 to 5.

Examples of a substituent that may substitute the linear or branched alkyl group having 1 to 12 carbon atoms represented by $R^{131}$ and $R^{132}$ in the general formula (m2-1) include those mentioned above in connection with the linear or branched alkyl group having 1 to 10 carbon atoms.

Examples of the aryl group having 6 to 12 carbon atoms represented by $R^{131}$ and $R^{132}$ include a phenyl group, a phenyl group that is substituted with a substituent mentioned above in connection with the linear or branched alkyl group having 1 to 10 carbon atoms, and the like.

The iodonium cations respectively represented by the following formulas (ii-1) to (ii-3) are preferable as the iodonium cation represented by the general formula (m2).

(ii-1)
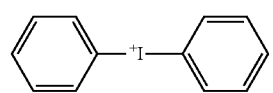

(ii-2)
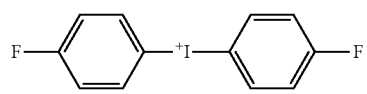

(ii-3)
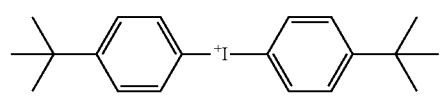

The sulfonium cations respectively represented by the formulas (i-1) and (i-6) to (i-13) and the iodonium cations respectively represented by the formulas (ii-1) and (ii-2) are particularly preferable as the monovalent onium cation.

The monovalent onium cation represented by $M^+$ included in the acid generator (A) may be produced by the method described in Advances in Polymer Science, vol. 62, pp. 1-48 (1984), for example.

The acid generator (A) included in the radiation-sensitive composition according to one embodiment of the invention generates an acid due to dissociation of the monovalent onium cation ($M^+$) upon exposure or heating. More specifically, the acid generator (A) generates a sulfonic acid represented by the following general formula (1a), and preferably generates a sulfonic acid represented by the following general formula (2a).

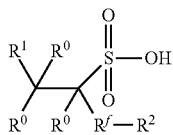
(1a)

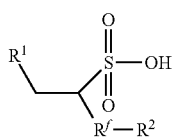
(2a)

$R^0$, $R^1$, $R^2$, and $R^f$ in the general formulas (1a) and (2a) are the same as defined for $R^0$, $R^1$, $R^2$, and $R^f$ in the general formulas (1) and (2). The description given above in connection with $R^0$, $R^1$, $R^2$, and $R^f$ in the general formulas (1) and (2) may be applied directly to $R^0$, $R^1$, $R^2$, and $R^f$ in the general formulas (1a) and (2a).

The acid generator (A) may be synthesized by an arbitrary method. For example, the acid generator (A) may be synthesized by reacting a compound represented by the following general formula (X1) or (X2) with a halide of a desired onium cation ($M^+$) (e.g., $M^+Br^-$) in an aqueous solution (see the following reaction formulas).

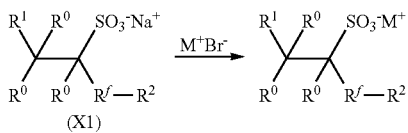
(X1)

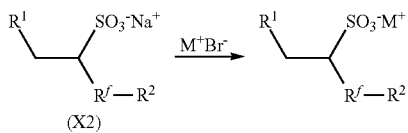
(X2)

$R^0$, $R^1$, $R^2$, $R^f$, and $M^+$ in the above reaction formulas are the same as defined for $R^0$, $R^1$, $R^2$, $R^f$, and $M^+$ in the general formulas (1) and (2). The description given above in connection with $R^0$, $R^1$, $R^2$, $R^f$, and $M^+$ in the general formulas (1) and (2) may be applied directly to $R^0$, $R^1$, $R^2$, $R^f$, and $M^+$ in the above reaction formulas.

The radiation-sensitive composition according to one embodiment of the invention may include only one type of the acid generator (A), or may include two or more types of the acid generator (A).

In the radiation-sensitive composition according to one embodiment of the invention, the content of the acid generator (A) is normally in the range from 0.1 to 50 parts by mass, preferably from 1 to 40 parts by mass, and more preferably from 5 to 30 parts by mass based on 100 parts by mass of a resin (B) and an acid-labile dissolution inhibitor compound (described below) in total. If the amount of the acid generator (A) is less than 0.1 parts by mass, the intended effects of the invention may not be sufficiently achieved. If the amount of the acid generator (A) exceeds 50 parts by mass, the transparency to radiation, the pattern shape, the heat resistance, and the like may deteriorate.

[1-2] Resin (B)

The radiation-sensitive composition according to one embodiment of the invention may further include a resin.

The resin (hereinafter may be referred to as "resin (B)") includes a repeating unit that includes an acid-labile group. The resin (B) is insoluble or scarcely soluble in an alkali, but becomes readily soluble in an alkali due to an acid. The expression "insoluble or scarcely soluble in an alkali" means that a film (thickness: 100 nm) formed only of the resin (B) has a thickness equal to or more than 50% of the initial thickness when developed under alkaline development conditions employed when forming a resist pattern using a resist film formed of a radiation-sensitive composition that includes the resin (B).

When the radiation-sensitive composition according to one embodiment of the invention includes the resin (B), the radiation-sensitive composition can produce a chemically-amplified positive-tone resist film that effectively responds to electron beams or extreme ultraviolet rays during a lithographic process, and can stably and accurately produce a fine pattern.

The acid-labile group included in the repeating unit included in the resin (B) dissociates due to an acid. The repeating unit is not particularly limited as long as the repeating unit has the above function, but is preferably at least one of a repeating unit represented by the following general formula (p-1) (hereinafter referred to as "repeating unit (p-1)") and a repeating unit represented by the following general formula (p-2) (hereinafter referred to as "repeating unit (p-2)").

Excellent sensitivity can be achieved by utilizing at least one of the repeating unit (p-1) and the repeating unit repeating unit (p-2) as the repeating unit that includes the acid-labile group.

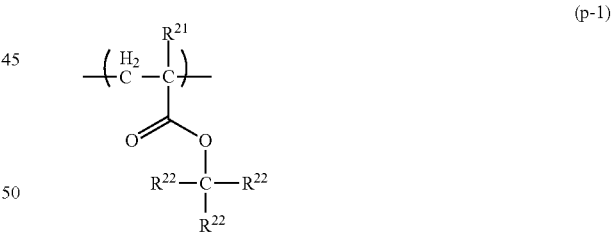
(p-1)

(In the general formula (p-1), $R^{21}$ represents a hydrogen atom, a methyl group, a trifluoromethyl group, or a hydroxymethyl group, and $R^{22}$ independently represent a linear or branched alkyl group having 1 to 4 carbon atoms, an aryl group having 6 to 22 carbon atoms, a monovalent alicyclic hydrocarbon group having 4 to 20 carbon atoms, or a group derived therefrom, or two of $R^{22}$ bond to each other to form a divalent alicyclic hydrocarbon group or a group derived therefrom together with the carbon atom that is bonded to the two $R^{22}$, and the remainder of $R^{22}$ represents a linear or branched alkyl group having 1 to 4 carbon atoms, an aryl group having 6 to 22 carbon atoms, a monovalent alicyclic hydrocarbon group having 4 to 20 carbon atoms, or a group derived therefrom.)

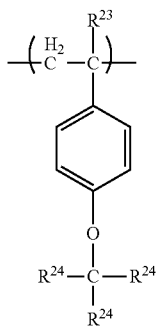

(p-2)

(x-1)

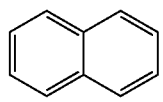
(x-2)

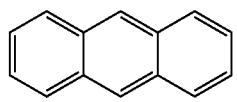
(x-3)

(In the general formula (p-2), $R^{23}$ represents a hydrogen atom, a methyl group, a trifluoromethyl group, or a hydroxymethyl group, and $R^{24}$ independently represent a linear or branched alkyl group having 1 to 4 carbon atoms, a monovalent alicyclic hydrocarbon group having 4 to 20 carbon atoms, or a group derived therefrom, or two of $R^{24}$ bond to each other to form a divalent alicyclic hydrocarbon group or a group derived therefrom together with the carbon atom that is bonded to the two $R^{24}$, and the remainder of $R^{24}$ represents a linear or branched alkyl group having 1 to 4 carbon atoms, a monovalent alicyclic hydrocarbon group having 4 to 20 carbon atoms, or a group derived therefrom.)

Examples of the linear or branched alkyl group having 1 to 4 carbon atoms represented by $R^{22}$ in the general formula (p-1) include a methyl group, an ethyl group, an n-propyl group, an i-propyl group, an n-butyl group, a 2-methylpropyl group, a 1-methylpropyl group, a t-butyl group, and the like.

Examples of the monovalent alicyclic hydrocarbon group having 4 to 20 carbon atoms represented by $R^{22}$ in the general formula (p-1) include a group that includes an alicyclic ring derived from a cycloalkane such as norbornane, tricyclodecane, tetracyclododecane, adamantane, cyclobutane, cyclopentane, cyclohexane, cycloheptane, or cyclooctane, and the like.

Examples of a group derived from the alicyclic hydrocarbon group include a group obtained by substituting the monovalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Examples of the aryl group having 6 to 22 carbon atoms represented by $R^{22}$ in the general formula (p-1) include groups derived from the structures respectively represented by the following formulas (x-1) to (x-3). When $R^{22}$ represents a group (i.e., naphthyl group) derived from the structure represented by the formula (x-2), $R^{22}$ may be bonded to the carbon atom included in —O—C($R^{22}$)$_3$ in the general formula (p-1) (i.e., the carbon atom that is bonded to the oxygen atom) at the 1-position or 2-position. When $R^{22}$ represents a group (i.e., anthryl group) derived from the structure represented by the formula (x-3), $R^{22}$ may be bonded to the carbon atom included in —O—C($R^{22}$)$_3$ in the general formula (p-1) at the 1-position, 2-position, or 9-position.

The aryl group may be substituted with a substituent. Specific examples of the substituent include a methyl group, an ethyl group, a hydroxyl group, a carboxyl group, a halogen atom (e.g., fluorine atom, chlorine atom, and bromine atom), an alkoxy group (e.g., methoxy group, ethoxy group, propoxy group, and butoxy group), an alkyloxycarbonyl group, and the like.

Examples of the divalent alicyclic hydrocarbon group that is formed by two of $R^{22}$ together with the carbon atom that is bonded to the two $R^{22}$ (i.e., the carbon atom bonded to the oxygen atom) include a divalent alicyclic hydrocarbon group having 4 to 20 carbon atoms, and the like. Specific examples of the divalent alicyclic hydrocarbon group include a group that includes an alicyclic ring derived from norbornane, tricyclodecane, tetracyclododecane, adamantane, cyclopentane, or cyclohexane, and the like.

Examples of a group derived from the divalent alicyclic hydrocarbon group formed by two of $R^{22}$ include a group obtained by substituting the divalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

The repeating unit represented by the general formula (p-1) is preferably any of repeating units represented by the following general formulas (p-1-1) to (p-1-7), and more preferably the repeating unit represented by the following general formula (p-1-2), (p-1-3), or (p-1-4). When the resin (B) includes the repeating unit represented by the general formula (p-2-1), the resulting resist pattern exhibits a small degree of nano edge roughness.

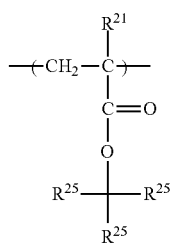
(p-1-1)

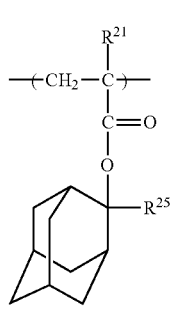
(p-1-2)

(p-1-3)
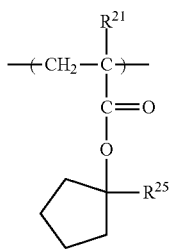

(p-1-4)
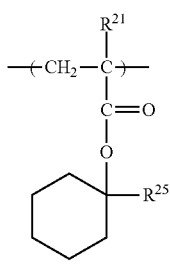

(p-1-5)
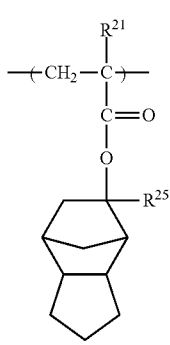

(p-1-6)
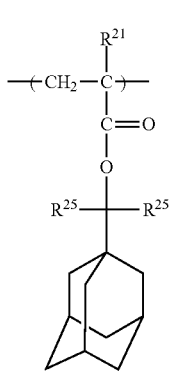

(p-1-7)
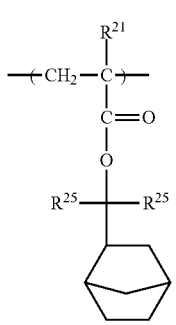

(In the general formulas (p-1-1) to (p-1-7), $R^{21}$ represents a hydrogen atom, a methyl group, a trifluoromethyl group, or a hydroxymethyl group, and $R^{25}$ independently represent a linear or branched alkyl group having 1 to 4 carbon atoms or an aryl group having 6 to 22 carbon atoms.)

The description given above in connection with the linear or branched alkyl group having 1 to 4 carbon atoms or the aryl group having 6 to 22 carbon atoms represented by $R^{22}$ in the general formula (p-1) may be applied directly to the linear or branched alkyl group having 1 to 4 carbon atoms or the aryl group having 6 to 22 carbon atoms represented by $R^{25}$ in the general formulas (p-1-1) to (p-1-7).

The resin (B) may include only one type of the repeating unit (p-1), or may include two or more types of the repeating unit (p-1).

The description given above in connection with the linear or branched alkyl group having 1 to 4 carbon atoms, the monovalent alicyclic hydrocarbon group having 4 to 20 carbon atoms, or a group derived therefrom represented by $R^{22}$ in the general formula (p-1), the divalent alicyclic hydrocarbon group formed by two of $R^{22}$ together with the carbon atom that is bonded to the two $R^{22}$, or a group derived therefrom may be applied directly to the linear or branched alkyl group having 1 to 4 carbon atoms, the monovalent alicyclic hydrocarbon group having 4 to 20 carbon atoms, or a group derived therefrom represented by $R^{24}$ in the general formula (p-2), the divalent alicyclic hydrocarbon group formed by two of $R^{24}$ together with the carbon atom that is bonded to the two $R^{24}$, or a group derived therefrom.

The repeating unit (p-2) is preferably a repeating unit represented by the following general formula (p-2-1). When the resin (B) includes the repeating unit represented by the general formula (p-2-1), the resulting resist pattern exhibits a small degree of nano edge roughness.

(p-2-1)
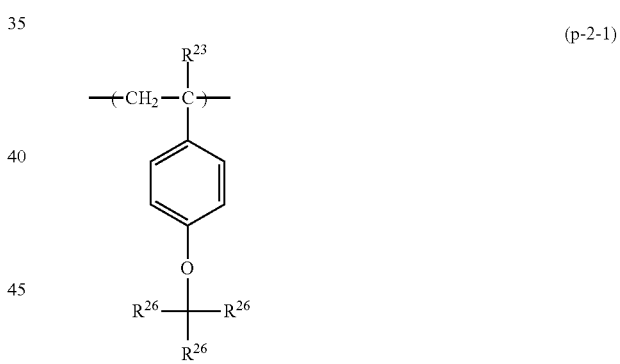

(In the general formula (p-2-1), $R^{23}$ represents a hydrogen atom, a methyl group, a trifluoromethyl group, or a hydroxymethyl group, and $R^{26}$ independently represent a linear or branched alkyl group having 1 to 4 carbon atoms.)

The description given above in connection with the linear or branched alkyl group having 1 to 4 carbon atoms represented by $R^{22}$ in the general formula (p-1) may be applied directly to the linear or branched alkyl group having 1 to 4 carbon atoms represented by $R^{26}$ in the general formula (p-2-1).

The resin (B) may include only one type of the repeating unit (p-2), or may include two or more types of the repeating unit (p-2).

The resin (B) preferably includes at least one of repeating units respectively represented by the following general formulas (b-1) to (b-5) in addition to the repeating units (p-1) and (p-2).

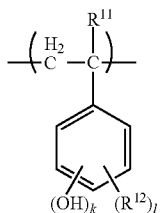
(b-1)

(In the general formula (b-1), $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, provided that $k+l \leq 5$ is satisfied.)

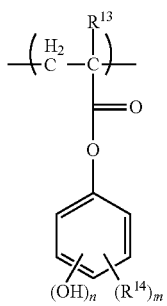
(b-2)

(In the general formula (b-2), $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, provided that $m+n \leq 5$ is satisfied.)

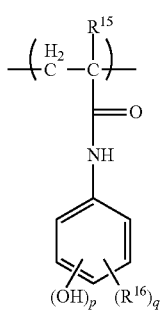
(b-3)

(In the general formula (b-3), $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, provided that $p+q \leq 5$ is satisfied.)

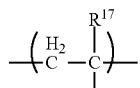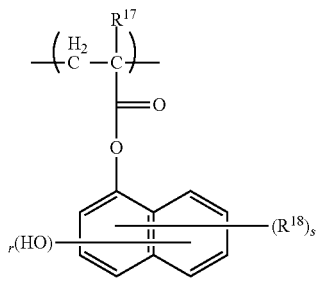
(b-4)

(In the general formula (b-4), $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3.)

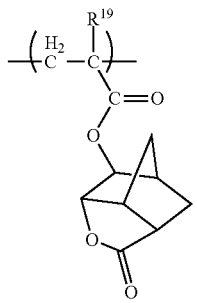
(b-5)

(In the general formula (b-5), $R^{19}$ represents a hydrogen atom or a methyl group.)

When the resin (B) includes the repeating unit represented by the general formula (b-1) (hereinafter referred to as "repeating unit (b-1)"), the resulting resist pattern exhibits a small degree of nano edge roughness.

Examples of the linear or branched alkyl group having 1 to 12 carbon atoms represented by $R^{12}$ in the general formula (b-1) include a methyl group, an ethyl group, an n-propyl group, an i-propyl group, an n-butyl group, a 2-methylpropyl group, a 1-methylpropyl group, a t-butyl group, and the like. Among these, a methyl group, an ethyl group, an n-butyl group, and a t-butyl group are preferable since the nano edge roughness can be reduced.

Examples of the linear or branched alkoxy group having 1 to 12 carbon atoms represented by $R^{12}$ in the general formula (b-1) include a methoxy group, an ethoxy group, an n-propoxy group, an i-propoxy group, an n-butoxy group, a 2-methylpropoxy group, a 1-methylpropoxy group, a t-butoxy group, and the like. Among these, a methoxy group and an ethoxy group are preferable since the nano edge roughness can be reduced.

k in the general formula (b-1) is an integer from 0 to 3, and preferably 1 or 2. l is an integer from 0 to 3, and preferably from 0 to 2.

Specific examples of the repeating unit (b-1) include the repeating units respectively represented by the following formulas (b-1-1) to (b-1-4), and the like.

The resin (B) may include only one type of the repeating unit (b-1), or may include two or more types of the repeating unit (b-1).

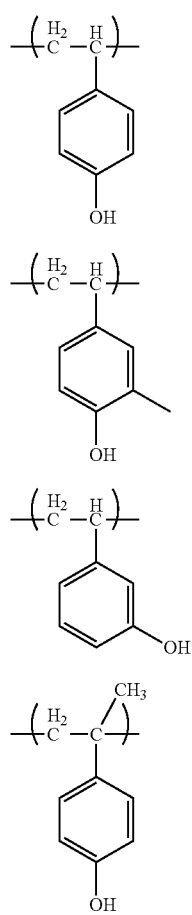

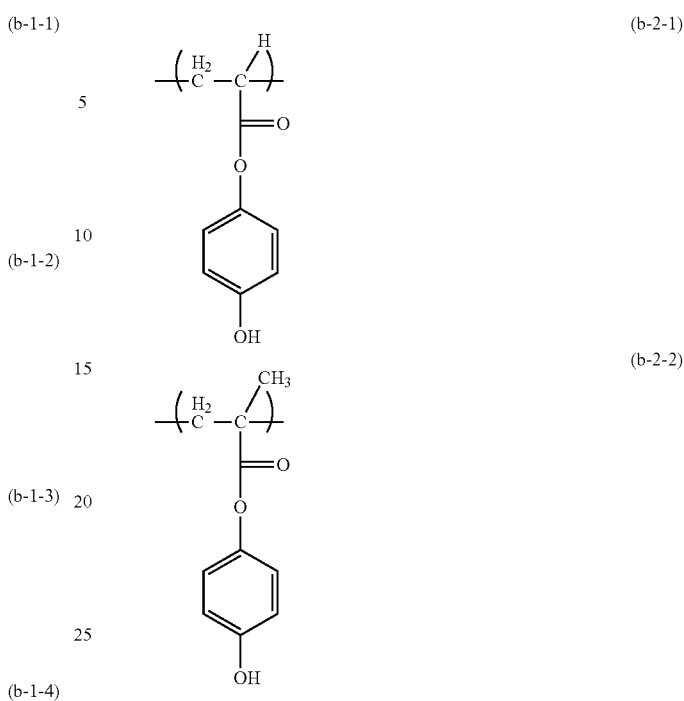

The repeating unit (b-1) may be obtained using the corresponding hydroxystyrene derivative as a monomer. The repeating unit (b-1) may also be obtained using a compound that produces the corresponding hydroxystyrene derivative via hydrolysis as a monomer.

Examples of the monomer used to produce the repeating unit (b-1) include p-acetoxystyrene, p-(1-ethoxy)styrene, p-isopropenylphenol, and the like. When using p-acetoxystyrene, the repeating unit (b-1) is produced by polymerizing p-acetoxystyrene, and hydrolyzing the side chain of the resulting polymer.

When the resin (B) includes the repeating unit represented by the general formula (b-2) (hereinafter referred to as "repeating unit (b-2)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{14}$ in the general formula (b-2) include those mentioned above in connection with the linear or branched alkyl group having 1 to 12 carbon atoms or the linear or branched alkoxy group having 1 to 12 carbon atoms represented by $R^{12}$ in the general formula (b-1).

m in the general formula (b-2) is an integer from 0 to 3, and preferably 0 or 1. n is an integer from 0 to 3, and preferably 1 or 2.

Specific examples of the repeating unit (b-2) include the repeating units respectively represented by the following formulas (b-2-1) and (b-2-2), and the like.

The resin (B) may include only one type of the repeating unit (b-2), or may include two or more types of the repeating unit (b-2).

The repeating unit (b-2) may be obtained using the corresponding monomer.

Examples of the monomer used to produce the repeating unit (b-2) include 4-hydroxyphenyl acrylate, 4-hydroxyphenyl methacrylate, and the like.

When the resin (B) includes the repeating unit represented by the general formula (b-3) (hereinafter referred to as "repeating unit (b-3)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{16}$ in the general formula (b-3) include those mentioned above in connection with the linear or branched alkyl group having 1 to 12 carbon atoms or the linear or branched alkoxy group having 1 to 12 carbon atoms represented by $R^{12}$ in the general formula (b-1).

p in the general formula (b-3) is an integer from 0 to 3, and preferably 1 or 2. q is an integer from 0 to 3, and preferably 0 or 1.

Specific examples of the repeating unit (b-3) include the repeating units respectively represented by the following formulas (b-3-1) and (b-3-2), and the like.

The resin (B) may include only one type of the repeating unit (b-3), or may include two or more types of the repeating unit (b-3).

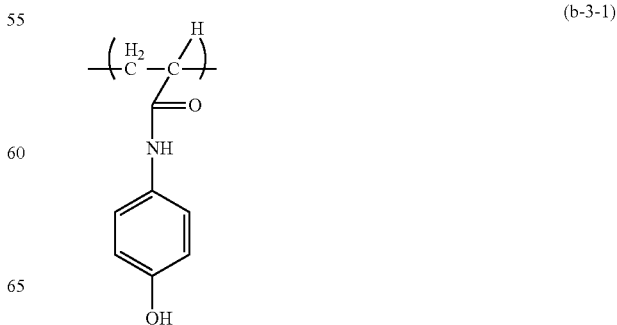

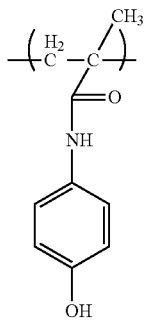
(b-3-2)

The repeating unit (b-3) may be obtained using the corresponding monomer.

Examples of the monomer used to produce the repeating unit (b-3) include N-(4-hydroxyphenyl)acrylamide, N-(4-hydroxyphenyl)methacrylamide, and the like.

When the resin (B) includes the repeating unit represented by the general formula (b-4) (hereinafter referred to as "repeating unit (b-4)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{18}$ in the general formula (b-4) include those mentioned above in connection with the linear or branched alkyl group having 1 to 12 carbon atoms or the linear or branched alkoxy group having 1 to 12 carbon atoms represented by $R^{12}$ in the general formula (b-1).

r in the general formula (b-4) is an integer from 0 to 3, and preferably 1 or 2. s is an integer from 0 to 3, and preferably 0 or 1.

Specific examples of the repeating unit (b-4) include the repeating units respectively represented by the following formulas (b-4-1) and (b-4-2), and the like.

The resin (B) may include only one type of the repeating unit (b-4), or may include two or more types of the repeating unit (b-4).

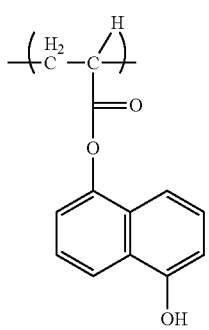
(b-4-1)

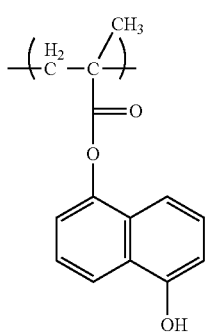
(b-4-2)

The repeating unit (b-3) may be obtained using the corresponding monomer.

Examples of the monomer used to produce the repeating unit (b-4) include 5-hydroxynaphthalen-1-yl methacrylate, 5-hydroxynaphthalen-1-yl acrylate, and the like.

When the resin (B) includes the repeating unit represented by the general formula (b-5) (hereinafter referred to as "repeating unit (b-5)"), the resulting resist pattern exhibits a small degree of nano edge roughness.

Specific examples of the repeating unit (b-5) include the repeating units respectively represented by the following formulas (b-5-1) and (b-5-2), and the like.

The resin (B) may include only one type of the repeating unit (b-5), or may include two or more types of the repeating unit (b-5).

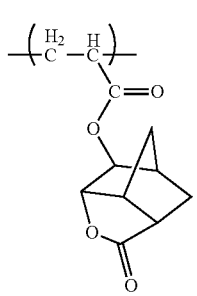
(b-5-1)

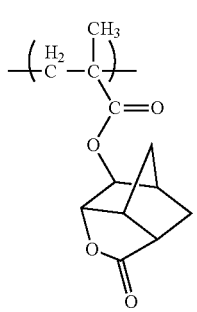
(b-5-2)

The resin (B) may further include a repeating unit derived from a non-acid-labile compound (i.e., a compound that does not include a group that dissociates due to an acid (acid-labile group)) (hereinafter referred to as "repeating unit (b-6)") in addition to the repeating units (p-1), (p-2), and (b-1) to (b-5).

When the resin (B) includes the repeating unit (b-6), the resulting resist pattern exhibits a small degree of nano edge roughness.

Examples of the non-acid-labile compound that produces the repeating unit (b-6) include styrene, α-methylstyrene, 4-methylstyrene, 2-methylstyrene, 3-methylstyrene, isobornyl acrylate, tricyclodecanyl (meth)acrylate, tetracyclododecenyl (meth)acrylate, and the like. Among these, styrene, α-methylstyrene, 4-methylstyrene, 2-methylstyrene, 3-methylstyrene, and tricyclodecanyl acrylate are preferable.

The resin (B) may include only one type of the repeating unit (b-6), or may include two or more types of the repeating unit (b-6).

The content of the repeating unit that includes the acid-labile group (particularly the total content of the repeating units (p-1) and (p-2)) in the resin (B) is preferably 1 mol % or more, more preferably in the range from 10 to 70 mol %, and further preferably from 20 to 60 mol % based on the total amount (=100 mol %) of the repeating units included in the resin (B). If the content of the repeating unit that includes the acid-labile group is less than 1 mol %, nano edge roughness may occur to a large extent. When the content of the repeating unit that includes the acid-labile group is 1 mol % or more (particularly 10 to 70 mol %), a resist film that exhibits a small degree of nano edge roughness can be formed.

The total content of the repeating units (b-1) to (b-5) in the resin (B) is preferably 95 mol % or less, more preferably in the range from 1 to 95 mol %, further preferably from 10 to 95 mol %, and particularly from 40 to 80 mol % based on the total amount (=100 mol %) of the repeating units included in the resin (B). If the total content of the repeating units (b-1) to (b-5) exceeds 95 mol %, nano edge roughness may occur to a large extent. When the content of the repeating unit that includes the acid-labile group is 1 mol % or more, a resist film that exhibits a small degree of nano edge roughness can be formed.

The total content of the repeating units (p-1), (p-2), and (b-1) to (b-5) in the resin (B) is preferably 10 mol % or more, more preferably in the range from 40 to 100 mol %, and further preferably from 50 to 100 mol % based on the total amount (=100 mol %) of the repeating units included in the resin (B). If the total content of the repeating units (p-1), (p-2), and (b-1) to (b-5) is less than 10 mol %, nano edge roughness may occur to a large extent. When the content of the repeating unit that includes the acid-labile group is 10 mol % or more, a resist film that exhibits a small degree of nano edge roughness can be formed.

The content of the repeating unit (b-6) in the resin (B) is preferably 60 mol % or less, and more preferably in the range from 0 to 50 mol % based on the total amount (=100 mol %) of the repeating units included in the resin (B). If the content of the repeating unit (b-6) exceeds 60 mol %, nano edge roughness may occur to a large extent. When the content of the repeating unit (b-6) is 60 mol % or less, a resist film that exhibits high resolution and a small degree of nano edge roughness in a well-balanced manner can be formed.

The resin (B) may be produced (synthesized) by an arbitrary method. For example, the resin (B) may be produced by radical polymerization or anionic polymerization. The side-chain phenol or naphthol moiety of the repeating units (b-1) to (b-4) may be obtained by hydrolyzing the resulting resin (B) (e.g., acetoxy group) in an organic solvent in the presence of a base or an acid.

The polystyrene-reduced weight average molecular weight (hereinafter may be referred to as "Mw") of the resin (B) determined by gel permeation chromatography (GPC) is preferably in the range from 3,000 to 100,000, more preferably from 3,000 to 40,000, and further preferably from 3.000 to 25,000.

The ratio (dispersity) (Mw/Mn) of the Mw to the polystyrene-reduced number average molecular weight (hereinafter may be referred to as "Mn") of the resin (B) determined by GPC is preferably 1 to 5, more preferably 1 to 3, and further preferably 1 to 2.5.

The radiation-sensitive composition according to one embodiment of the invention may include only one type of the resin (B), or may include two or more types of the resin (B).

[1-3] Acid-labile Dissolution Inhibitor Compound

The radiation-sensitive composition according to one embodiment of the invention may further include an acid-labile dissolution inhibitor compound.

The acid-labile dissolution inhibitor compound is a compound that includes at least two acid-labile groups (i.e., a group that is decomposed due to an acid) in its structure.

Examples of a preferable acid-labile dissolution inhibitor compound include compounds obtained by protecting some or all of the phenolic OH groups of the polyhydroxy compounds disclosed in Japanese Patent Application Publication (KOKAI) No. 1-289946, Japanese Patent Application Publication (KOKAI) No. 1-289947, Japanese Patent Application Publication (KOKAI) No. 2-2560, Japanese Patent Application Publication (KOKAI) No. 3-128959, Japanese Patent Application Publication (KOKAI) No. 3-158855, Japanese Patent Application Publication (KOKAI) No. 3-179353, Japanese Patent Application Publication (KOKAI) No. 3-191351, Japanese Patent Application Publication (KOKAI) No. 3-200251, Japanese Patent Application Publication (KOKAI) No. 3-200252, Japanese Patent Application Publication (KOKAI) No. 3-200253, Japanese Patent Application Publication (KOKAI) No. 3-200254, Japanese Patent Application Publication (KOKAI) No. 3-200255, Japanese Patent Application Publication (KOKAI) No. 3-259149, Japanese Patent Application Publication (KOKAI) No. 3-279958, Japanese Patent Application Publication (KOKAI) No. 3-279959, Japanese Patent Application Publication (KOKAI) No. 4-1650, Japanese Patent Application Publication (KOKAI) No. 4-1651, Japanese Patent Application Publication (KOKAI) No. 4-11260, Japanese Patent Application Publication (KOKAI) No. 4-12356, Japanese Patent Application Publication (KOKAI) No. 4-12357, Japanese Patent Application Publication (KOKAI) No. 4-271349, Japanese Patent Application Publication (KOKAI) No. 5-045869, Japanese Patent Application Publication (KOKAI) No. 5-158233, Japanese Patent Application Publication (KOKAI) No. 5-224409, Japanese Patent Application Publication (KOKAI) No. 5-257275, Japanese Patent Application Publication (KOKAI) No. 5-297581, Japanese Patent Application Publication (KOKAI) No. 5-297583, Japanese Patent Application Publication (KOKAI) No. 5-303197, Japanese Patent Application Publication (KOKAI) No. 05-303200, Japanese Patent Application Publication (KOKAI) No. 5-341510, and the like with an acid-labile group.

Further examples of the acid-labile dissolution inhibitor compound include the compounds disclosed in Japanese Patent Application Publication (KOKAI) No. 2009-222920, and the like.

[1-4] Acid Diffusion Controller

The radiation-sensitive composition according to one embodiment of the invention preferably further includes an acid diffusion controller (hereinafter may be referred to as "acid diffusion controller (C)") in addition to the acid generator (A), the resin (B), and the acid-labile dissolution inhibitor compound.

The acid diffusion controller (C) controls a phenomenon in which an acid generated by the acid generator (A) upon exposure is diffused in the resist film, and suppresses undesired chemical reactions in the unexposed area.

The storage stability of the resulting radiation-sensitive composition is improved by adding the acid diffusion controller (C) to the radiation-sensitive composition. Moreover, the acid diffusion controller (C) improves the resolution of the resulting resist, and suppresses a change in line width of the resist pattern due to a change in post-exposure delay (PED) from exposure to post-exposure bake, so that a radiation-sensitive composition that exhibits remarkably superior process stability can be obtained.

Examples of the acid diffusion controller (C) include nitrogen-containing organic compounds and photosensitive basic compounds.

Examples of the nitrogen-containing organic compounds include a compound represented by the following general formula (4) (hereinafter referred to as "nitrogen-containing compound (i)"), a compound that includes two nitrogen atoms in the molecule (hereinafter referred to as "nitrogen-containing compound (ii)"), a polyamino compound or a polymer that includes three or more nitrogen atoms (hereinafter collectively referred to as "nitrogen-containing compound (iii)"), an amide group-containing compound, a urea compound, a nitrogen-containing heterocyclic compound, and the like.

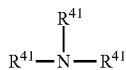
(4)

In the general formula (4), $R^{41}$ independently represent a hydrogen atom, a substituted or unsubstituted linear, branched or cyclic alkyl group, a substituted or unsubstituted aryl group, or a substituted or unsubstituted aralkyl group.

Examples of the nitrogen-containing compound (i) include mono(cyclo)alkylamines such as n-hexylamine, n-heptylamine, n-octylamine, n-nonylamine, n-decylamine, and cyclohexylamine, di(cyclo)alkylamines, tri(cyclo)alkylamines, substituted alkylamines such as triethanolamine, and aromatic amines Examples of the nitrogen-containing compound (II) include compounds that include two nitrogen atoms in one molecule (e.g., diamines and imidazolidinones), and the like.

Examples of the nitrogen-containing compound (iii) include polyethyleneimine, polyallylamine, poly(2-dimethylaminoethylacrylamide), and the like.

Examples of the amide group-containing compound include N-t-butoxycarbonyl group-containing amino compounds, formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl)isocyanurate, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles, pyridines, piperazines, pyrazine, pyrazole, pyridazine, quinoxaline, purine, pyrrolidine, piperidine, piperidineethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, and the like.

The photosensitive basic compound is not particularly limited as long as the photosensitive basic compound has the above properties. Examples of the photosensitive basic compound include compounds respectively represented by the following general formulas (5-1) and (5-2), and the like.

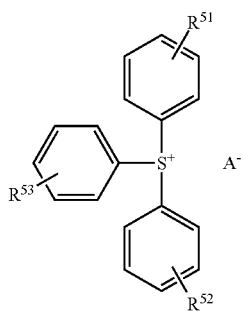
(5-1)

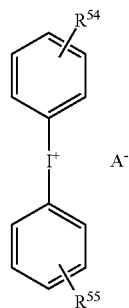
(5-2)

In the general formula (5-1), $R^{51}$ to $R^{53}$ independently represent a hydrogen atom, a halogen atom, a substituted or unsubstituted alkyl group having 1 to 10 carbon atoms, a substituted or unsubstituted alicyclic hydrocarbon group, —$OSO_2$—$R^{56}$, or —$SO_2$—$R^{57}$ (wherein $R^{56}$ and $R^{57}$ represent a substituted or unsubstituted alkyl group having 1 to 10 carbon atoms, a substituted or unsubstituted alicyclic hydrocarbon group, or a substituted or unsubstituted aryl group), provided that two or more of $R^{51}$ to $R^{53}$ may bond to form a cyclic structure, and $A^-$ represents $OH^-$, $R^{58}O^-$, or $R^{58}COO^-$ (wherein $R^{58}$ represents a monovalent organic group).

In the general formula (5-2), $R^{54}$ and $R^{55}$ independently represent a hydrogen atom, a halogen atom, a substituted or unsubstituted alkyl group having 1 to 10 carbon atoms, or a substituted or unsubstituted alicyclic hydrocarbon group, and $A^-$ represents $OH^-$, $R^{59}O^-$, or $R^{59}COO^-$ (wherein $R^{59}$ represents a monovalent organic group).

Examples of the halogen atom represented by $R^{51}$ to $R^{53}$ in the general formula (5-1) include a fluorine atom, a bromine atom, and the like.

Examples of the unsubstituted alkyl group having 1 to 10 carbon atoms represented by $R^{51}$ to $R^{57}$ in the general formulas (5-1) and (5-2) include a methyl group, an ethyl group, an n-propyl group, an i-propyl group, an n-butyl group, a 2-methylpropyl group, a 1-methylpropyl group, a t-butyl group, and the like.

Note that the alkyl group may be substituted with a hydroxyl group, a carboxyl group, a halogen atom (e.g., fluorine atom or bromine atom), an alkoxy group (e.g., methoxy group, ethoxy group, propoxy group, butoxy group, or t-butoxy group), an alkyloxycarbonyl group (e.g., t-butoxycarbonylmethyloxy group), or the like.

Examples of the unsubstituted alicyclic hydrocarbon group represented by $R^{51}$ to $R^{57}$ include an alicyclic hydrocarbon group having 5 to 25 carbon atoms, and the like. Specific examples of the unsubstituted alicyclic hydrocarbon group represented by $R^{51}$ to $R^{57}$ include a cyclopentyl group, a cyclohexyl group, and the like.

Note that the alicyclic hydrocarbon group may be substituted with a hydroxyl group, a carboxyl group, a halogen atom (e.g., fluorine atom or bromine atom), an alkoxy group (e.g., methoxy group, ethoxy group, propoxy group, butoxy group, or t-butoxy group), an alkyloxycarbonyl group (e.g., t-butoxycarbonylmethyloxy group), or the like.

Examples of the unsubstituted aryl group represented by $R^{56}$ and $R^{57}$ include an aryl group having 6 to 12 carbon atoms, and the like. Specific examples of the unsubstituted aryl group represented by $R^{56}$ and $R^{57}$ include a phenyl group, a naphthyl group, and the like.

The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

$R^{51}$ to $R^{55}$ in the general formulas (5-1) and (5-2) preferably represent a hydrogen atom, a methyl group, or a t-butyl group.

Examples of the monovalent organic group represented by $R^{58}$ and $R^{59}$ in $A^-$ in the general formulas (5-1) and (5-2) include a substituted or unsubstituted alkyl group, a substituted or unsubstituted aryl group, and the like.

$A^-$ preferably represents $OH^-$, $CH_3COO^-$, or any of the compounds respectively represented by the following formulas (6-1) to (6-5).

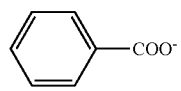
(6-1)

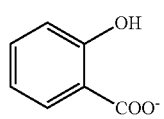
(6-2)

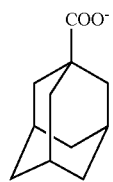
(6-3)

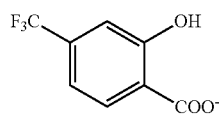
(6-4)

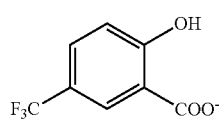
(6-5)

The photosensitive basic compound is preferably a triphenylsulfonium compound (i.e., the compound represented by the general formula (5-1)) wherein the anion moiety ($A^-$) is $OH^-$, $CH_3COO^-$, or the compound represented by the formula (6-2), (6-3) or (6-4).

These acid diffusion controllers (C) may be used either alone or in combination.

The content of the acid diffusion controller (C) is preferably 15 parts by mass or less, more preferably in the range from 0.001 to 10 parts by mass, and further preferably from 0.005 to 5 parts by mass based on 100 parts by mass of the resin (B) and the acid-labile dissolution inhibitor compound in total. If the amount of the acid diffusion controller (C) exceeds 15 parts by mass, the sensitivity of the resulting resist film or the developability of the exposed area may deteriorate. If the amount of the acid diffusion controller (C) is less than 0.001 parts by mass, the pattern shape or the dimensional accuracy of the resulting resist film may deteriorate depending on the process conditions.

[1-5] Additional Photoacid Generator

The radiation-sensitive composition according to one embodiment of the invention may further include an additional photoacid generator other than the acid generator (A) (hereinafter may be referred to as "additional acid generator").

Examples of the additional acid generator include onium salt compounds, sulfonic acid compounds, and the like (excluding compounds that fall under the acid generator (A)).

Among these additional acid generators, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl-2-oxocyclohexylmethylsulfonium trifluoromethanesulfonate, dicyclohexyl-2-oxocyclohexylsulfonium trifluoromethanesulfonate, 2-oxocyclohexyldimethylsulfonium trifluoromethanesulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic acid imide trifluoromethanesulfonate, triphenylsulfonium nonafluorobutanesulfonate, triphenylsulfonium trifluoromethanesulfonate, triphenylsulfonium 2-bicyclo[2.2.1]hept-2-yl-1,1-difluoroethanesulfonate, triphenylsulfonium 2-bicyclo[2.2.1]hept-2-yl-1,1,2,2-tetrafluoroethanesulfonate, 4-butoxy-1-naphthyltetrahydrothiophenium nonafluorobutanesulfonate, and 4-butoxy-1-naphthyltetrahydrothiophenium 2-bicyclo[2.2.1]hept-2-yl-1,1,2,2-tetrafluoroethanesulfonate are preferable.

These additional acid generators may be used either alone or in combination.

The additional acid generator is used in an amount of preferably 0 to 80 parts by mass, and more preferably 0 to 50 parts by mass based on 100 parts by mass of the acid generator (A) in order to ensure that a resist film formed using the resulting radiation-sensitive composition exhibits excellent sensitivity and developability. If the amount of the additional acid generator exceeds 80 parts by mass, the resolution of the radiation-sensitive composition may deteriorate.

[1-6] Additional Component

The radiation-sensitive composition according to one embodiment of the invention may further include a solvent or an additive (e.g., surfactant, sensitizer, or aliphatic additive) in addition to the acid generator (A), the resin (B), the acid diffusion controller (C), and the additional acid generator.

Examples of the solvent include ethylene glycol monoalkyl ether acetates, propylene glycol monoalkyl ethers, propylene glycol dialkyl ethers, propylene glycol monoalkyl ether acetates, lactates, formates, acetates, propionates, other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, 3-methyl-3-methoxybutyl butyrate, methyl acetoacetate, ethyl acetoacetate, methyl pyruvate, and ethyl pyruvate, aromatic hydrocarbons, ketones, amides, lactones, and the like. These solvents may be used either alone or in combination.

It is preferable that the radiation-sensitive composition include at least one compound selected from ethylene glycol monoalkyl ether acetates and propylene glycol monoalkyl ether acetates as the solvent from the viewpoint of applicability.

The radiation-sensitive composition preferably includes at least one compound selected from ethylene glycol monoalkyl ether acetates and propylene glycol monoalkyl ether acetates in an amount of preferably 70 to 100 parts by mass, and more preferably 70 to 80 parts by mass based on 100 parts by mass of the solvent in total.

The solvent is used so that the radiation-sensitive composition has a total solid content of preferably 1 to 70 mass %, more preferably 1 to 15 mass %, and further preferably 1 to 10 mass %. If the solvent is used so that the total solid content is within the above range, it is possible to prevent a situation in which the applicability of the radiation-sensitive composition is impaired due to an increase in viscosity. This makes it possible to form a resist film having a sufficient thickness.

The radiation-sensitive composition according to one embodiment of the invention may be prepared by homogeneously dissolving the acid generator (A) and the resin (B) in the solvent optionally together with the acid diffusion controller (C), the additional acid generator, and an additive (e.g., surfactant or sensitizer) so that the total solid content is within the above range. The radiation-sensitive composition thus prepared is preferably filtered through a filter having a pore size of about 0.2 µm, for example.

The surfactant improves the applicability, striation, developability, and the like of the radiation-sensitive composition.

The surfactant is preferably used in an amount of preferably 2 parts by mass or less, and more preferably 0.001 to 2 parts by mass based on 100 parts by mass of the resin (B) and the acid-labile dissolution inhibitor compound in total.

The sensitizer absorbs the energy of radiation, and transmits the energy to the acid generator (A), so that the amount of acid generated increases. Specifically, the sensitizer improves the apparent sensitivity of the radiation-sensitive composition.

The sensitizer is preferably used in an amount of preferably 20 parts by mass or less, and more 0.1 to 20 parts by mass based on 100 parts by mass of the resin (B) and the acid-labile dissolution inhibitor compound in total.

A dye or a pigment visualizes the latent image in the exposed area, and reduces the effects of halation during exposure. An adhesion improver improves the adhesion of the resist film to a substrate.

An alicyclic additive improves the dry etching resistance, the pattern shape, the adhesion to a substrate, and the like.

Examples of the alicyclic additive include adamantane derivatives, deoxycholates, lithocholates, 3-[2-hydroxy-2,2-bis(trifluoromethyl)ethyl]tetracyclo[6.2.1.1$^{3,6}$.0$^{2,7}$]dodecane, and the like. These alicyclic additives may be used either alone or in combination.

Examples of further additives include an alkali-soluble polymer, a low-molecular-weight alkali solubility controller that includes an acid-labile protecting group, a halation inhibitor, a preservative, an antifoaming agent, and the like.

[2] Resist Pattern-Forming Method

The radiation-sensitive composition according to one embodiment of the invention may be useful as a material for forming a chemically-amplified positive-tone resist film. For example, when forming a chemically-amplified positive-tone resist film using the radiation-sensitive composition that includes the resin (B), the acid-labile group included in the resin (B) dissociates due to an acid generated by the acid generator (A) upon exposure, so that the resin (B) becomes alkali-soluble. Specifically, an alkali-soluble area is formed in the resist film. The alkali-soluble area corresponds to the exposed area of the resist. The exposed area can be dissolved and removed using an alkaline developer. A positive-tone resist pattern having a desired shape can thus be obtained. The resist pattern-forming method is described in detail below.

When forming a resist pattern using the radiation-sensitive composition according to one embodiment of the invention, a resist film is formed using the radiation-sensitive composition.

The radiation-sensitive composition can be prepared by filtering a solution of which the total solid content has been adjusted to become a desired value through a filter with a pore size of about 0.2 µm. The radiation-sensitive composition is applied to a substrate (e.g., silicon wafer or silicon dioxide-coated wafer) by an appropriate application method (e.g., rotational coating, cast coating, or roll coating) to form a resist film. After that, the resist film may optionally be heated (PB) at a temperature ranging from about 70° C. to 160° C.

The resist film is then exposed so that a desired resist pattern is formed. Examples of radiation for exposure include (extreme) deep ultraviolet rays such as KrF excimer laser light (wavelength: 248 nm), ArF excimer laser light (wavelength: 193 nm), EUV light (extreme ultraviolet rays, wavelength: 13.5 nm), X-rays such as synchrotron radiation, charged particle rays such as electron beams, and the like. The exposure conditions (e.g., dose) may be appropriately selected depending on the composition of the radiation-sensitive composition, the type of additive, and the like. Note that liquid immersion lithography may also be used.

The resist film is preferably subjected to heat treating (PEB) after exposure. PEB ensures smooth dissociation of the acid-labile group included in the resin (B). The heating condition of PEB is appropriately selected depending on the composition of the radiation-sensitive resin composition, but is preferably in the range from 30° C. to 200° C., and more preferably from 50° C. to 170° C.

In order to maximize the potential of the radiation-sensitive resin composition, an organic or inorganic antireflective film may be formed on the substrate (see Japanese Examined Patent Publication (KOKOKU) No. 6-12452 (Japanese Patent Application Publication (KOKAI) No. 59-93448), for example). A protective film may be formed on the resist film so that the resist film is not affected by basic impurities and the like contained in the environmental atmosphere (see Japanese Patent Application Publication (KOKAI) No. 5-188598, for example). Note that these techniques may be used in combination.

The exposed resist film is developed to form a given resist pattern. The developer for development is preferably an alkaline aqueous solution in which at least one alkaline compound of sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, 1,5-diazabicyclo-[4.3.0]-5-nonene, and the like is dissolved.

The concentration of the alkaline aqueous solution is preferably 10 mass % or less. If the concentration of the alkaline aqueous solution exceeds 10 mass %, the unexposed area may also be dissolved in the developer.

The pH of the developer is preferably in the range from 8 to 14, and more preferably from 9 to 14.

An organic solvent may be added to the alkaline aqueous solution (developer). Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methyl alcohol, ethyl alcohol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide, and the like. These organic solvents may be used either individually or in combination.

The organic solvent is preferably used in an amount of 100 parts or less by volume based on 100 parts by volume of the alkaline aqueous solution. If the amount of the organic solvent exceeds 100 parts by volume, the exposed area may remain undeveloped due to a decrease in developability. An appropriate amount of a surfactant and the like may also be added to the alkaline aqueous solution (developer). After development using the alkaline aqueous solution (developer), the resist film is normally washed with water, and dried.

[3] Novel Compound

A novel compound according to one embodiment of the invention is represented by the general formula (1) (preferably the general formula (2)).

The description given above in connection with the compound represented by the general formula (1) or (2) that is used as the acid generator (A) included in the radiation-sensitive composition according to one embodiment of the invention may be applied directly to the novel compound according to one embodiment of the invention.

The novel compound according to one embodiment of the invention exhibits high solubility in a solvent, and may suitably be used as the acid generator (A) that is included in the radiation-sensitive composition according to one embodiment of the invention.

EXAMPLES

The embodiments of the invention are further described below by way of examples, however, the present invention is in no way limited by these examples without departing from the scope of the invention. In the following examples, electron beams (EB) were used to expose the resist film. The present invention is in no way limited by these Examples. In addition, "part" and "%" in the description are based on weight unless otherwise indicated. Note that similar basic resist properties are obtained using short-wavelength radiation (e.g., EUV), and a correlation is observed between the basic resist properties obtained using electron beams (EB) and the basic resist properties obtained using short-wavelength radiation (e.g., EUV).

[1] Synthesis of Resin

Synthesis Example 1

Synthesis of Resin (B-1)

55 g of p-acetoxystyrene, 45 g of the compound represented by the following formula (M-1) (hereinafter may be referred to as "compound (M-1)"), 4 g of azobisisobutylonitrile, and 1 g of t-dodecylmercaptan were dissolved in 100 g of propylene glycol monomethyl ether. The compounds were polymerized at 70° C. for 16 hours in a nitrogen atmosphere. After completion of polymerization, the reaction mixture was added dropwise to 1000 g of n-hexane to coagulate and purify the copolymer. After the addition of 150 g of propylene glycol monomethyl ether to the copolymer, 150 g of methanol, 34 g of triethylamine, and 6 g of water were added to the mixture. The mixture was hydrolyzed at the boiling point for 8 hours under reflux. After completion of the reaction, the solvent and triethylamine were evaporated under reduced pressure. After dissolving the copolymer in 150 g of acetone, the solution was added dropwise to 2000 g of water to coagulate the copolymer. A white powder thus produced was filtered off, and dried at 50° C. overnight under reduced pressure.

The resulting copolymer had an Mw of 10,000 and a dispersity (Mw/Mn) of 2.1. The molar ratio of repeating units derived from p-hydroxystyrene and repeating units derived from the compound (M-1) in the copolymer determined by $^{13}$C-NMR analysis was 65:35. This copolymer is hereinafter referred to as "resin (B-1)".

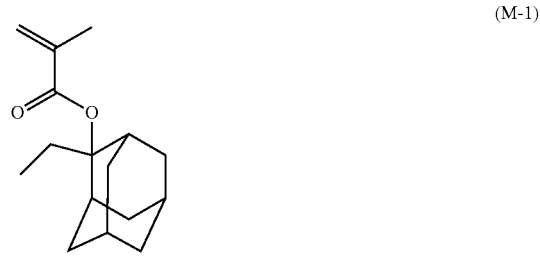

(M-1)

Synthesis Example 2

Synthesis of Resin (B-2)

53 g of p-acetoxystyrene, 47 g of the compound represented by the following formula (M-2) (hereinafter may be referred to as "compound (M-2)"), 4 g of azobisisobutylonitrile, and 0.2 g of t-dodecylmercaptan were dissolved in 200 g of propylene glycol monomethyl ether. The compounds were polymerized at 70° C. for 6 hours in a nitrogen atmosphere. After completion of polymerization, the reaction mixture was added dropwise to 2000 g of n-hexane to coagulate and purify the copolymer. After the addition of 150 g of propylene glycol monomethyl ether to the copolymer, 150 g of methanol, 37 g of triethylamine, and 7 g of water were added to the mixture. The mixture was hydrolyzed at the boiling point for 8 hours under reflux. After completion of the reaction, the solvent and triethylamine were evaporated under reduced pressure. After dissolving the resulting copolymer in 150 g of acetone, the solution was added dropwise to 2000 g of water to coagulate the copolymer. A white powder thus produced was filtered off, and dried at 50° C. overnight under reduced pressure.

The resulting copolymer had an Mw of 13,000 and a dispersity (Mw/Mn) of 2.4. The molar ratio of repeating units derived from p-hydroxystyrene and repeating units derived from the compound (M-2) in the copolymer determined by $^{13}$C-NMR analysis was 50:50. This copolymer is hereinafter referred to as "resin (B-2)".

(M-2)

Synthesis Example 3

Synthesis of Resin (B-3)

55 g of the compound represented by the following formula (M-3) (hereinafter may be referred to as "compound (M-3)"), 45 g of the compound represented by the following formula (M-4) (hereinafter may be referred to as "compound (M-4)"), and 3 g of azobisisobutylonitrile were dissolved in 300 g of methyl ethyl ketone. The compounds were polymerized at 78° C. for 6 hours in a nitrogen atmosphere. After completion of polymerization, the reaction mixture was added dropwise to 2000 g of methanol to coagulate and purify the copolymer. The copolymer (white powder) was washed twice with 300 g of methanol, filtered off, and dried at 50° C. overnight under reduced pressure.

The resulting copolymer had an Mw of 7000 and a dispersity (Mw/Mn) of 2.1. The molar ratio of repeating units derived from the compound (M-3) and repeating units derived from the compound (M-4) in the copolymer determined by $^{13}$C-NMR analysis was 47:53. This copolymer is hereinafter referred to as "resin (B-3)".

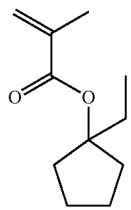
(M-3)

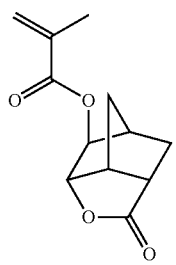
(M-4)

Note that the weight average molecular weight (Mw) and the number average molecular weight (Mn) were determined by gel permeation chromatography (GPC) using GPC columns manufactured by Tosoh Corporation (G2000HXL×2, G3000HXL×1, G4000HXL×1) (flow rate: 1.0 ml/min, eluant: tetrahydrofuran, column temperature: 40° C., standard: monodisperse polystyrene). The dispersity (Mw/Mn) was calculated from the measurement results.

The copolymer was subjected to $^{13}$C-NMR analysis using a mass spectrometer "JNM-EX270" (manufactured by JEOL Ltd.).

[2] Preparation of Radiation-sensitive Composition

Example 1

100 parts of the resin (B-1) obtained in Synthesis Example 1, 20 parts of an acid generator (A-1), 2 parts of an acid diffusion controller (C-1), 1400 parts of a solvent (D-1), and 3300 parts of a solvent (D-2) were mixed (see Table 1). The mixture was filtered through a membrane filter (pore size: 200 nm) to obtain a composition solution (radiation-sensitive composition of Example 1).

Examples 2 to 8 and Comparative Example 1

The resin (B), the acid generator (A), the acid diffusion controller (C), and the solvent (D) were mixed in the ratio shown in Table 1. The resulting mixture was filtered through a membrane filter (pore size: 200 nm) to obtain a composition solution (radiation-sensitive compositions of Examples 2 to 8 and Comparative Example 1).

TABLE 1

| | Resin (B) | | Acid generator (A) | | Acid diffusion controller (C) | | Solvent (D) | |
|---|---|---|---|---|---|---|---|---|
| | Type | Amount (parts) | Type | Amount (parts) | Type | Amount (parts) | Type | Amount (parts) |
| Example 1 | B-1 | 100 | A-1 | 20 | C-1 | 2 | D-1 | 1400 |
| | | | | | | | D-2 | 3300 |
| Example 2 | B-2 | 100 | A-1 | 20 | C-2 | 3 | D-1 | 1400 |
| | | | | | | | D-2 | 3300 |
| Example 3 | B-2 | 100 | A-2 | 20 | C-2 | 3 | D-1 | 1400 |
| | | | | | | | D-2 | 3300 |
| Example 4 | B-3 | 100 | A-1 | 20 | C-1 | 2 | D-1 | 1400 |
| | | | | | | | D-2 | 3300 |
| Example 5 | B-3 | 100 | A-1 | 20 | C-2 | 3 | D-1 | 1400 |
| | | | | | | | D-2 | 3300 |
| Example 6 | B-3 | 100 | A-2 | 20 | C-2 | 3 | D-1 | 1400 |
| | | | | | | | D-2 | 3300 |
| Example 7 | B-2 | 100 | A-4 | 20 | C-2 | 3 | D-1 | 1400 |
| | | | | | | | D-2 | 3300 |
| Example 8 | B-2 | 100 | A-5 | 20 | C-2 | 3 | D-1 | 1400 |
| | | | | | | | D-2 | 3300 |
| Comparative Example 1 | B-1 | 100 | A-3 | 14 | C-1 | 2 | D-1 | 1400 |
| | | | | | | | D-2 | 3300 |

The details of the acid generator (A), the resin (B), the acid diffusion controller (C), and the solvent (D) shown in Table 1 are shown below.

Acid Generator (A)
(A-1) to (A-5): compounds respectively represented by the following formulas (A-1) to (A-5)

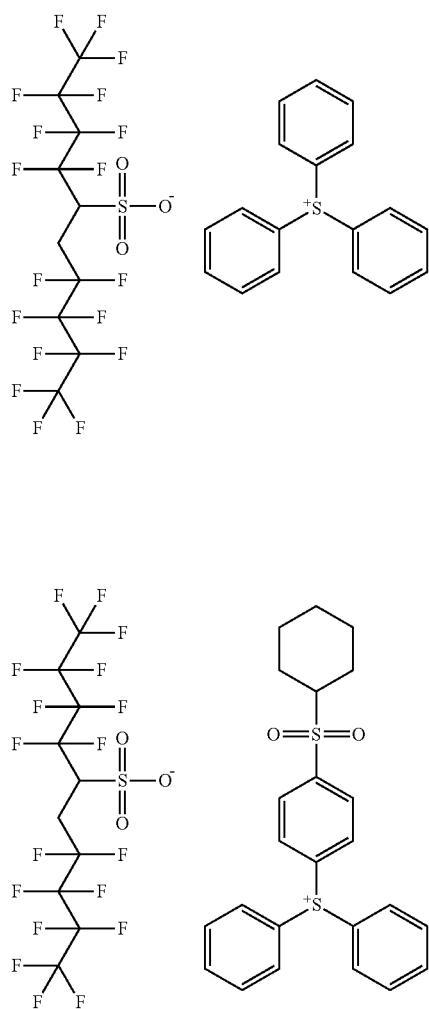

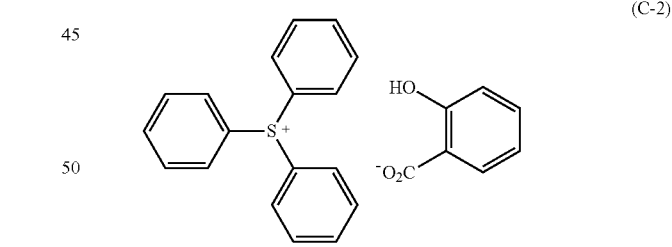

Resin (B)
(B-1): resin (B-1) obtained in Synthesis Example 1
(B-2): resin (B-2) obtained in Synthesis Example 2
(B-3): resin (B-3) obtained in Synthesis Example 3
Acid Diffusion Controller (C)
(C-1): tri-n-octylamine
(C-2): compound represented by the following formula (C-2)

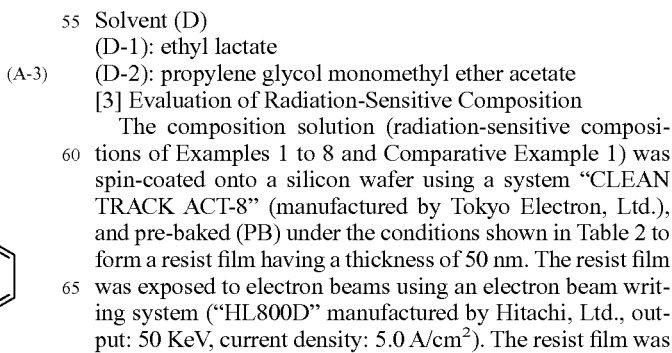

Solvent (D)
(D-1): ethyl lactate
(D-2): propylene glycol monomethyl ether acetate

[3] Evaluation of Radiation-Sensitive Composition

The composition solution (radiation-sensitive compositions of Examples 1 to 8 and Comparative Example 1) was spin-coated onto a silicon wafer using a system "CLEAN TRACK ACT-8" (manufactured by Tokyo Electron, Ltd.), and pre-baked (PB) under the conditions shown in Table 2 to form a resist film having a thickness of 50 nm. The resist film was exposed to electron beams using an electron beam writing system ("HL800D" manufactured by Hitachi, Ltd., output: 50 KeV, current density: $5.0 \text{ A/cm}^2$). The resist film was then subjected to post-exposure bake (PEB) under the conditions shown in Table 2. The resist film subjected to PEB was developed at 23° C. for 1 minute by a puddle method using a 2.38% tetramethylammonium hydroxide aqueous solution, rinsed with purified water, and dried to obtain a resist pattern.

The resist pattern thus obtained was evaluated as described below. The evaluation results are shown in Table 2.

(1) Sensitivity (L/S)

A dose at which a line-and-space pattern (1L1S) including a line area (width: 130 nm) and a space area (groove) (width: 130 nm) defined by the adjacent line areas was formed at a 1:1 line width was determined to be an optimum dose, and the sensitivity was evaluated based on the optimum dose.

(2) Nano Edge Roughness

Figure 2:
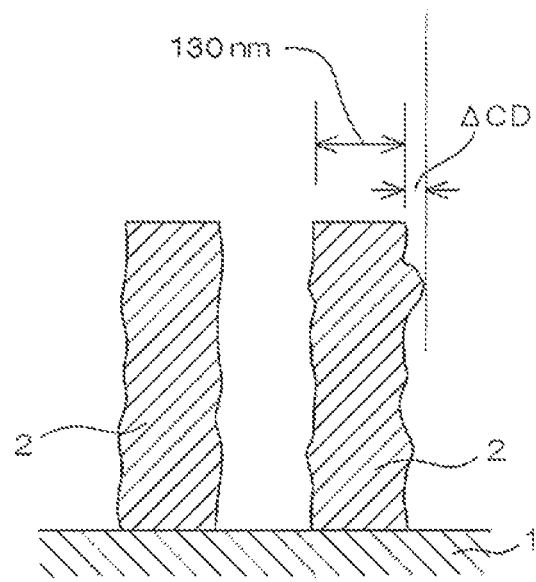
FIG. 2 is a schematic cross-sectional view illustrating the shape of a line pattern.

The line pattern of a line-and-space pattern (1L1S) (design line width: 130 nm) was observed using a scanning electron microscope ("S-9220" manufactured by Hitachi, Ltd.). The nano edge roughness was evaluated by determining the difference "ΔCD" between the design line width (130 nm) and the line width in an area where elevations and depressions significantly occurred along a side 2a of a line area 2 of a resist film formed on a silicon wafer 1 (see FIGS. 1 and 2) using a CD-scanning electron microscope (SEM) ("S-9220" manufactured by Hitachi High-Technologies Corporation). Note that elevations and depressions are exaggerated in FIGS. 1 and 2.

(3) Resolution (L/S)

The minimum line width (nm) of the line pattern of a line-and-space pattern (1L1S) that was resolved at the optimum dose was taken as the resolution.

pound according to the embodiment of the present invention may be suitable as an acid generator included in the radiation-sensitive composition.

Since the radiation-sensitive composition according to the embodiments of the invention exhibits high resolution when forming a line-and-space resist pattern and shows only a small degree of nano edge roughness, the radiation-sensitive composition may be useful for forming a fine pattern using EB, EUV, or X-rays. Therefore, the radiation-sensitive composition may be useful as a material for forming a chemically-amplified resist for producing semiconductor devices that are expected to be further miniaturized in the future.

The invention claimed is:

1. A radiation-sensitive composition comprising:
a photoacid generator represented by formula (2); and
a solvent,

wherein $R^1$ represents
a linear or branched hydrocarbon group having 1 to 30 carbon atoms, some or all of the hydrogen atoms of the hydrocarbon group represented by $R^1$ being substituted with a fluorine atom,

TABLE 2

| | PB condition | | PEB condition | | Sensitivity | Nano edge | Resolution |
|---|---|---|---|---|---|---|---|
| | Temperature (° C.) | Time (seconds) | Temperature (° C.) | Time (seconds) | ($\mu C/cm^2$) | roughness (nm) | (nm) |
| Example 1 | 120 | 60 | 100 | 60 | 36.0 | 11 | 70 |
| Example 2 | 120 | 60 | 100 | 60 | 32.0 | 10 | 60 |
| Example 3 | 120 | 60 | 100 | 60 | 31.0 | 9 | 60 |
| Example 4 | 120 | 60 | 110 | 60 | 37.0 | 12 | 70 |
| Example 5 | 120 | 60 | 110 | 60 | 32.0 | 10 | 60 |
| Example 6 | 120 | 60 | 110 | 60 | 32.0 | 9 | 60 |
| Example 7 | 120 | 60 | 100 | 60 | 33.0 | 10 | 70 |
| Example 8 | 120 | 60 | 100 | 60 | 32.0 | 10 | 70 |
| Comparative Example 1 | 120 | 60 | 100 | 60 | 36.0 | 10 | 90 |

As is clear from Table 2, it was confirmed that the radiation-sensitive compositions of Examples 1 to 8 containing the acid generator (A-1), (A-2), (A-4), or (A-5) could produce a chemically-amplified positive-tone resist film that effectively responds to electron beams or extreme ultraviolet rays, shows only a small degree of roughness and excellent resolution, and accurately and stably produces a fine pattern, as compared with the radiation-sensitive composition of Comparative Example 1 that contained the acid generator (A-3) instead of the acid generator (A-1), (A-2), (A-4), or (A-5).

A radiation-sensitive composition and a novel compound according to the embodiment of the invention may be used for photolithography employed in the production of semiconductor devices (e.g., IC), liquid crystal devices, circuit boards (e.g., thermal head), and the like. More specifically, a radiation-sensitive composition according to the embodiment of the present invention may suitably be used for photolithography that utilizes an exposure light source having a wavelength of 220 nm or less (e.g., deep ultraviolet rays (e.g., ArF excimer laser light) or electron beams), and a novel comwherein $R^2$ represents a fluorine atom or a substituted or unsubstituted organic group, $R^f$ represents a linear or branched fluoroalkylene group having 2 to 30 carbon atoms, $M^+$ represents a monovalent onium cation, and optionally $R^1$ bonds to $R^f$ or $R^2$ to form a cyclic structure, and wherein the monovalent onium cation ($M^+$) is a sulfonium cation represented by formula (m1-1),

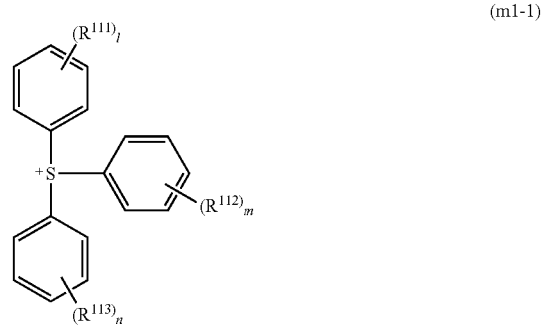

wherein each of $R^{111}$ to $R^{113}$ independently represents a hydroxyl group, a halogen atom, a substituted or unsubstituted alkyl group, a substituted or unsubstituted cycloalkyl group, a substituted or unsubstituted alkoxy group, —S—$R^{114}$, or —SO$_2$—$R^{115}$, l is an integer from 1 to 5, m is an integer from 0 to 5, and n is an integer from 0 to 5, wherein $R^{114}$ represents a substituted or unsubstituted alkyl group or a substituted or unsubstituted aryl group, wherein $R^{115}$ represents a substituted or unsubstituted alkyl group, a substituted or unsubstituted cycloalkyl group, a substituted or unsubstituted alkoxy group, or a substituted or unsubstituted aryl group, and wherein at least one $R^{111}$ represents —SO$_2$—$R^{115}$.

2. The radiation-sensitive composition according to claim 1, further comprising a resin that comprises at least one repeating unit among repeating units respectively represented by formulas (b-1) to (b-5),

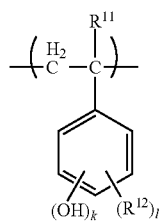

(b-1)

wherein $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, wherein k+l≤5 is satisfied,

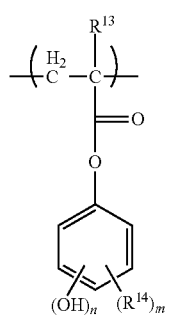

(b-2)

wherein $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, wherein m+n≤5 is satisfied,

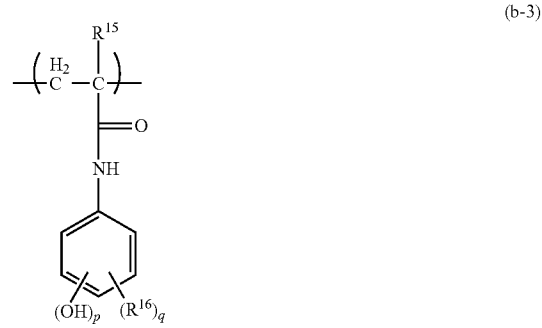

(b-3)

wherein $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, wherein p+q≤5 is satisfied,

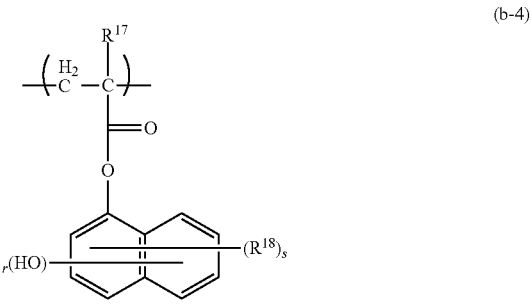

(b-4)

wherein $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3,

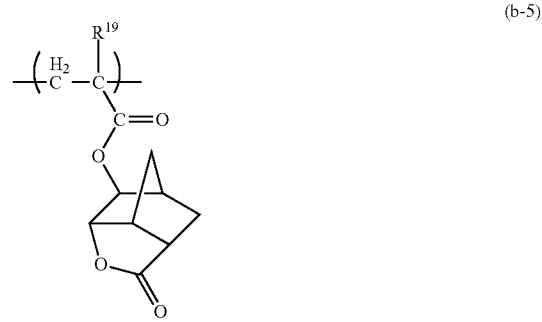

(b-5)

wherein $R^{19}$ represents a hydrogen atom or a methyl group.

3. The radiation-sensitive composition according to claim 1, wherein in the formula (2), $R^1$ represents CF$_3$—, $R^2$ represents a fluorine atom, and $R'$ represents —CF$_2$—.

4. The radiation-sensitive composition according to claim 1, wherein in the formula (2), $R^1$ represents C$_4$F$_9$—, $R^2$ represents a fluorine atom, and $R'$ represents —C$_4$F$_8$—.

5. The radiation-sensitive composition according to claim 1, further comprising a photosensitive basic compound which comprises a compound represented by formula (5-1), a compound represented by formula (5-2), or both thereof:

(5-1)

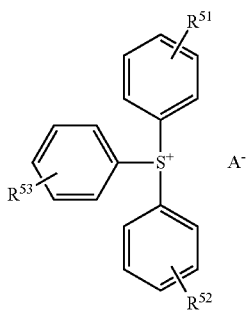

(5-2)

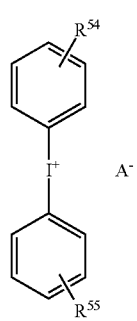

wherein, in the formula (5-1), $R^{51}$ to $R^{53}$ independently represent a hydrogen atom, a halogen atom, a substituted or unsubstituted alkyl group having 1 to 10 carbon atoms, a substituted or unsubstituted alicyclic hydrocarbon group, $-OSO_2-R^{56}$, or $-SO_2-R^{57}$, wherein $R^{56}$ and $R^{57}$ represent a substituted or unsubstituted alkyl group having 1 to 10 carbon atoms, a substituted or unsubstituted alicyclic hydrocarbon group, or a substituted or unsubstituted aryl group, and two or more of $R^{51}$ to $R^{53}$ optionally bond to form a cyclic structure, and $A^-$ represents $OH^-$, $R^{58}O^-$, or $R^{58}COO^-$, wherein $R^{58}$ represents a monovalent organic group, and wherein, in the formula (5-2), $R^{54}$ and $R^{55}$ independently represent a hydrogen atom, a halogen atom, a substituted or unsubstituted alkyl group having 1 to 10 carbon atoms, or a substituted or unsubstituted alicyclic hydrocarbon group, and $A^-$ represents $OH^-$, $R^{59}O^-$, or $R^{59}COO^-$, wherein $R^{59}$ represents a monovalent organic group.

6. The radiation-sensitive composition according to claim 5, wherein, in the formulas (5-1) and (5-2), $A^-$ represents a compound represented by formulas (6-1) to (6-5):

(6-1)

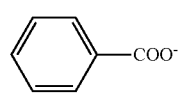

(6-2)

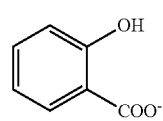

(6-3)

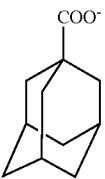

(6-4)

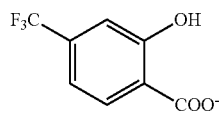

(6-5)

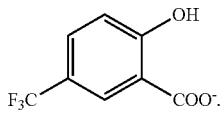

7. A compound represented by formula (2), (2)

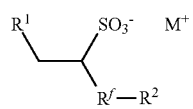

wherein $R^1$ represents a linear or branched hydrocarbon group having 1 to 30 carbon atoms, some or all of the hydrogen atoms of the hydrocarbon group represented by $R^1$ being substituted with a fluorine atom, wherein $R^2$ represents a fluorine atom or a substituted or unsubstituted organic group, $R^f$ represents a linear or branched fluoroalkylene group having 2 to 30 carbon atoms, $M^+$ represents a monovalent onium cation, and optionally $R^1$ bonds to $R^f$ or $R^2$ to form a cyclic structure, and wherein the monovalent onium cation ($M^+$) is a sulfonium cation represented by formula (m1-1), (m1-1)

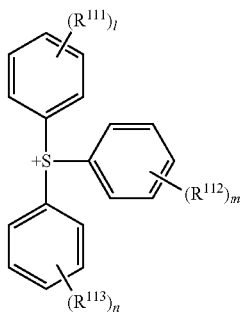

wherein each of $R^{111}$ to $R^{113}$ independently represents a hydroxyl group, a halogen atom, a substituted or unsubstituted alkyl group, a substituted or unsubstituted cycloalkyl group, a substituted or unsubstituted alkoxy group, $-S-R^{114}$, or $-SO_2-R^{115}$, l is an integer from 1 to 5, m is an integer from 0 to 5, and n is an integer from 0 to 5, wherein $R^{114}$ represents a substituted or unsubstituted alkyl group or a substituted or unsubstituted aryl group, wherein $R^{115}$ represents a substituted or unsubstituted alkyl group, a substituted or unsubstituted cycloalkyl group, a substituted or unsubstituted alkoxy group, or a substituted or unsubstituted aryl group, and wherein at least one $R^{111}$ represents —$SO_2$—$R^{115}$.

8. The compound according to claim 7, wherein in the formula (2), $R^1$ represents $CF_3$—, $R^2$ represents a fluorine atom, and $R^f$ represents —$CF_2$—.

9. The compound according to claim 7, wherein in the formula (2), $R^1$ represents $C_4F_9$—, $R^2$ represents a fluorine atom, and $R^f$ represents —$C_4F_8$—.

* * * * *